United States Patent
Kiga

(10) Patent No.: US 10,139,415 B2
(45) Date of Patent: Nov. 27, 2018

(54) METHOD FOR PREDICTING RESPONSIVENESS TO COMPOUND INHIBITING MAPK SIGNAL TRANSDUCTION PATHWAY

(71) Applicant: DAIICHI SANKYO COMPANY, LIMITED, Tokyo (JP)

(72) Inventor: Masaki Kiga, Tokyo (JP)

(73) Assignee: DAIICHI SANKYO COMPANY, LIMITED, Tokyo (JP)

(*) Notice: Subject to any disclaimer, the term of this patent is extended or adjusted under 35 U.S.C. 154(b) by 124 days.

(21) Appl. No.: 14/770,474

(22) PCT Filed: Feb. 27, 2014

(86) PCT No.: PCT/JP2014/054846
§ 371 (c)(1),
(2) Date: Aug. 26, 2015

(87) PCT Pub. No.: WO2014/133071
PCT Pub. Date: Sep. 4, 2014

(65) Prior Publication Data
US 2016/0011201 A1 Jan. 14, 2016

(30) Foreign Application Priority Data
Feb. 27, 2013 (JP) .................... 2013-036759

(51) Int. Cl.
*A61K 31/4468* (2006.01)
*G01N 33/574* (2006.01)
*A61K 31/00* (2006.01)
*C12Q 1/6886* (2018.01)
*C12Q 1/66* (2006.01)

(52) U.S. Cl.
CPC ....... *G01N 33/57496* (2013.01); *A61K 31/00* (2013.01); *A61K 31/4468* (2013.01); *C12Q 1/66* (2013.01); *C12Q 1/6886* (2013.01); *C12Q 2600/106* (2013.01); *C12Q 2600/156* (2013.01); *G01N 2333/4703* (2013.01)

(58) Field of Classification Search
None
See application file for complete search history.

(56) References Cited

U.S. PATENT DOCUMENTS

| 2005/0176016 A1 | 8/2005 | Park et al. |
| 2009/0233915 A1 | 9/2009 | Isshiki et al. |
| 2009/0239936 A1 | 9/2009 | Sugimoto et al. |
| 2010/0004233 A1 | 1/2010 | Iikura et al. |
| 2010/0209426 A1 | 8/2010 | Hollande et al. |

FOREIGN PATENT DOCUMENTS

| JP | WO 2004083167 A1 * | 9/2004 | ........... C07D 295/13 |
| WO | 00037141 A1 | 6/2000 | |
| WO | 02006213 A2 | 1/2002 | |
| WO | 03077914 A1 | 9/2003 | |
| WO | 2005121142 A1 | 12/2005 | |
| WO | 2006045514 A1 | 5/2006 | |
| WO | 2007014011 A2 | 2/2007 | |
| WO | 2007044515 A1 | 4/2007 | |
| WO | 2007096259 A1 | 8/2007 | |
| WO | 2010059503 A2 | 5/2010 | |

OTHER PUBLICATIONS

Kawanishi et al. Molecular and Cellular Biology, Mar. 1995, p. 1175-1181.*
Ludwig et al. "Biomarkers in Cancer Staging, Prognosis and Treatment Selection", Nature Reviews Cancer 2005 (5) 845-856.*
Wang et al. "Mutant proteins as cancer-specific biomarkers", PNAS 2011 (108) 2444-2449.*
Iwao et al. "Activation of the β-Catenin Gene by Interstitial Deletions Involving Exon 3 in Primary Colorectal Carcinomas without Adenomatous Polyposis Coli Mutations", Cancer Research 1998 (58) 1021-1026.*
Fang et al. "The MAPK signalling pathways and colorectal cancer", Lancet Oncology 2005 (6) 322-327.*
Ilyas et al. "β-Catenin mutations in cell lines established from human colorectal cancers", PNAS 1997 (94) 10330-10334.*
Wilhelm et al. "BAY 43-9006 Exhibits Broad Spectrum Oral Antitumor Activity and Targets the RAF/MEK/ERK Pathway and Receptor Tyrosine Kinases Involved in Tumor Progression and Angiogenesis", Cancer Research 2004 (64) 7099-7109.*
Mologni et al. "Synergistic Effects of Combined Wnt/KRAS Inhibition in Colorectal Cancer Cells", PLOS One 2012 (7) e51449, 1-10.*
Shama et al. "Major contribution of MEK1 to the activation of ERK1/ERK2 and to the growth of LS174T colon carcinoma cells", Biochemical and Biophysical Research Communications 2008 (372) 845-849.*

(Continued)

*Primary Examiner* — Jeffrey S Lundgren
*Assistant Examiner* — Michael J Schmitt
(74) *Attorney, Agent, or Firm* — Kilyk & Bowersox, P.L.L.C.

(57) ABSTRACT

Provided are: a method of predicting sensitivity to a molecularly targeted drug; a method of selecting a patient who is determined to have high responsiveness to administration of a drug; and a reagent to be used in these methods. Specifically, provided are: a method of predicting responsiveness to cancer disease treatment with a compound that inhibits a mitogen-activated protein kinase (hereinafter abbreviated as MAPK) signaling pathway, the method including using a biological sample derived from a cancer patient, measuring whether or not β-catenin contained in the biological sample has at least one kind of mutation selected from the group consisting of (i) an active mutation and (ii) a substitution mutation of an asparagine residue to a serine residue at position 287; a method of selecting a patient to be subjected to cancer disease treatment with the compound; a method of treating a cancer disease, the method including administering the compound to the patient selected by the above-mentioned method; and a reagent to be used in these methods.

5 Claims, 9 Drawing Sheets
Specification includes a Sequence Listing.

(56) References Cited

OTHER PUBLICATIONS

International Search Report and Written Opinion issued in corresponding International Patent Application No. PCT/JP2014/054846 dated Jun. 3, 2014 (4 pages).
Guardavaccaro et al., "Wnt/Beta-Catenin and MAPK Signaling: Allies and Enemies in Different Battlefields," Science Signaling, 2012, vol. 5, No. 219, pp. 1-2.
Ilyas et al., "Beta-Catenin mutations in cell lines established from human colorectal cancers," Proc. Natl. Acad. Sci. USA, 1997, vol. 94, pp. 10330-10334.
Kiga et al., "Antitumor effects of novel highly hydrophilic and non-ATP-competitive MEK1/2 inhibitor, SMK-17," Anti-Cancer Drugs, 2012, vol. 23, No. 1, pp. 119-130.
King et al., "Demonstration of a Genetic Therapeutic Index for Tumors Expressing Oncogenic BRAF by the Kinase Inhibitor SB-590885," Cancer Research, 2006, vol. 66, No. 23, pp. 11100-11105.
Morin et al., "Activation of Beta-Catenin-Tcf Signaling in Colon Cancer by Mutations in Beta-Catenin or APC." Science, 1997, vol. 275, No. 5307, pp. 1787-1790.
Tsujii et al., "Crosstalk between Wnt/beta-catenin system and MAPK system," Molecular Gastrointestinal Medicine, 2012, vol. 9, No. 3, pp. 261-266, (7 pages).
Aberle et al., "Beta-catenin is a target for the ubiquitin-proteasome pathway," The EMBO Journal, 1997, vol. 16, No. 20, pp. 3797-3804.
Alessi et al., "PD 098059 Is a Specific Inhibitor of the Activation of Mitogen-activated Protein Kinase Kinase in Vitro and in Vivo," The Journal of Biological Chemistry, 1995, vol. 270, No. 46, pp. 27489-27494.
Amit et al., "Axis-mediated CKI phosphorylation of beta-catenin at Ser 45: a molecular switch for the Wnt pathway," Genes & Development, 2002, vol. 16, No. 9, pp. 1066-1076.
Behrens et al., "Functional interaction of beta-catenin with the transcription factor LEF-1," Nature, 1996, vol. 382 (6592), pp. 638-642.
Boonstra et al., "The Epidermal Growth Factor," Cell Biology International, 1995, vol. 19, No. 5, pp. 413-430.
Bos et al., "Prevalence of ras gene mutations in human colorectal cancers," Nature, 1987, vol. 327 (6120), pp. 293-297.
Brose et al., "BRAF and RAS Mutations in Human Lung Cancer and Melanoma," Cancer Research, 2002, vol. 62 (23), pp. 6997-7000.
Cliffe et al., "A Role of Dishevelled in Relocating Axin to the Plasma Membrane during Wingless Signaling," Current Biology, 2003, vol. 13 (11), pp. 960-966.
Downward, J., "Targeting RAS Signalling Pathways in Cancer Therapy," Nature Reviews Cancer, 2003, vol. 3 (1), pp. 11-22.
Dummer et al., "AZD6244 (ARRY-142886) vs Temozolomide in Patients With Advanced Melanoma: An Open-Label, Randomized, Multicenter, Phase II Study," J. Clin. Oncol., 2008, vol. 26 (9033).
Favata et al., "Identification of a Novel Inhibitor of Mitogen-Activated Protein Kinase Kinase," The Journal of Biological Chemistry, 1998, vol. 273, No. 29, pp. 18623-18632.
Friday et al., "Advances in Targeting the Ras/Raf/MEK/Erk Mitogen-Activated Protein Kinase Cascade with MEK Inhibitors for Cancer Therapy," Clin Cancer Res, 2008, vol. 14, No. 2, pp. 342-346.
Hart et al., "Downregulation of beta-catenin by human Axin and its association with the APC tumor suppressor, beta-catenin and GSK3 beta," Current Biology, 1998, vol. 8, No. 10, pp. 573-581.
Hinoi et al., "Complex Formation of Adenomatous Polyposis Coli Gene Product and Axin Facilitates Glycogen Synthase Kinase-3 beta-dependent Phosphorylation of Beta-Catenin and Downregulates Beta-Catenin," The Journal of Biological Chemistry, 2000, vol. 275, No. 44, pp. 34399-34406.
Hoshino et al., "Constitutive activation of the 41-/43-kDa mitogen-activated protein kinase signaling pathway in human tumors," Oncogene, 1999, vol. 18, No. 3, pp. 813-822.
Hynes et al., "ERBB Receptors and Cancer: The Complexity of Targeted Inhibitors," Nature Reviews Cancer, 2005, vol. 5, No. 5, pp. 341-354.
Ikeda et al., "Axin, a negative regulator of the Wnt signaling pathway, forms a complex with GSK-3beta and beta-catenin and promotes GSK-3beta-dependent phosphorylation of beta-catenin," The EMBO Journal, 1998, vol. 17, No. 5, pp. 1371-1384.
Infante et al., "Safety and efficacy results from the first-in-human study of the oral MEK 1/2 inhibitor GSK1120212," Journal of Clinical Oncology, 2010, vol. 28, No. 15 (2503), 1 page.
Johnson et al., "Mitogen-Activated Protein Kinase Pathways Mediated by ERK, JNK, and p38 Protein Kinases," Science, 2002, vol. 298 (5600), pp. 1911-1912.
Kishida et al., "Axin, a Negative Regulator of the Wnt Signaling Pathway, Directly Interacts with Adenomatous Polyposis Coli and Regulates the Stabilization of Beta-Catenin," The Journal of Biological Chemistry, 1998, vol. 273, No. 18, pp. 10823-10826.
Lamlum et al., "The type of somatic mutation at APC in familial adenomatous polyposis is determined by the site of the germline mutation: a new facet to Knudson's 'two-hit' hypothesis," Nature Medicine, 1999, vol. 5, No. 9, pp. 1071-1075.
Latres et al., "The human F box protein beta-Trcp associates with the Cul1/Skp1 complex and regulates the stability of beta-catenin," Oncogene, 1999, vol. 18, No. 4, pp. 849-854.
Liu et al., "Beta-Trcp couples beta-catenin phosphorylation-degradation and regulates Xenopus axis formation," Proc. Natl. Acad. Sci. USA, 1999, vol. 96, No. 11, pp. 6273-6278.
Liu et al., "Control of beta-Catenin Phosphorylation/Degradation by a Dual-Kinase Mechanism," Cell, 2002, vol. 108, No. 6, pp. 837-847.
Lorusso et al., "A phase 1-2 clinical study of a second generation oral MEK inhibitor, PD 0325901 in patients with advanced cancer," Journal of Clinical Oncology, 2005 ASCO Annual Meeting Proceedings (Meeting Abstracts), 2005, vol. 23 (3011), No. 16S, (1 page).
Lynch et al., "Activating Mutations in the Epidermal Growth Factor Receptor Underlying Responsiveness of Non-Small-Cell Lung Cancer to Gefitinib," The New England Journal of Medicine, 2004, vol. 350, No. 21, pp. 2129-2139.
Malumbres et al., "RAS oncogenes: the first 30 years," Nature Reviews Cancer, 2003, vol. 3, No. 6, (pp. 459-465) pp. 7-13.
Miyaki et al., "Characteristics of Somatic Mutation of the Adenomatous Polyposis Coli Gene in Colorectal Tumors," Cancer Research, 1994, vol. 54, No. 11, pp. 3011-3020.
Molenaar et al., "XTcf-3 Transcription Factor Mediates Beta-Catenin-Induced Axis Formation in Xenopus Embryos," Cell, 1996, vol. 86, No. 3, pp. 391-399.
Polakis, P., "Wnt signal and cancer," Genes & Development, 2000, vol. 14, pp. 1837-1851.
Price, S. "Putative allosteric MEK1 and MEK2 inhibitors," Expert Opinion on Therapeutic Patents, 2008, vol. 18, No. 6, pp. 603-627.
Schlessinger, J., "Cell Signaling by Receptor Tyrosine Kinases," Cell, 2000, vol. 103 (2), pp. 211-225.
Sebolt-Leopold et al., "Blockade of the MAP kinase pathway suppresses growth of colon tumors in vivo," Nature Medicine, 1999, vol. 5, No. 7, pp. 810-816.
Sebolt-Leopold et al., "The biological profile of PD 0325901: A second generation analog of CI-1040 with improved pharmaceutical potential," Cancer Research, AACR Meeting Abstracts, 2004, vol. 64:925, (1 page).
Sieben et al., "In ovarian neoplasms, BRAF, but not KRAS, mutations are restricted to low-grade serous tumours," Journal of Pathology, 2004, vol. 202 (3), pp. 336-340.
Bout et al., BRAF mutation predicts sensitivity to MEK inhibition, Nature, 2006, vol. 439 (7074), No. 19, pp. 358-362.
Stephens et al., "Lung cancer: Intragenic ERBB2 kinase mutations in tumours," Nature, 2004, vol. 431 (7008), pp. 525-526.
Sumimoto et al., "Inhibition of growth and invasive ability of melanoma by inactivation of mutated BRAF with lentivirus-mediated RNA interference," Oncogene, 2004, vol. 23 (36), pp. 6031-6039.

(56) References Cited

OTHER PUBLICATIONS

Sunaga et al., "Constitutive Activation of the Wnt Signaling Pathway by CTNNBI (beta-Catenin) Mutations in a Subset of Human Lung Adenocarcinoma," Genes, Chromosomes & Cancer, 2001, vol. 30, pp. 316-321.
Takle et al., "The identification of potent and selective imidazole-based inhibitors of B-Raf kinase," Bioorganic Medicinal Chemistry Letters, 2006, vol. 16 (2), pp. 378-381.
Tamai et al., "A Mechanism for Wnt Coreceptor Activation," Molecular Cell, 2004, vol. 13 (1), pp. 149-156.
Trujillo, J. I., "MEK inhibitors: a patent review 2008-2010," Expert Opinion on Therapeutic Patents, 2011, vol. 21, No. 7, pp. 1045-1069.
Wallace et al., "Preclinical development of ARRY-142886, a potent and selective MEK inhibitor," Cancer Research, AACR Meeting Abstracts, 2004, vol. 64:897, (2 pages).
Wang et al., "Clinical experience of MEK inhibitors in cancer therapy," Biochimica et Biophysica Acta, 2007, 1773 (8), pp. 1248-1255.
Wilhelm et al., "Discovery and development of sorafenib: a multikinase inhibitor for treating cancer," Nature Reviews Drug Discovery, 2006, vol. 5 (18), pp. 835-844.
Xing, M., "BRAF mutation in thyroid cancer," Endocrine-Related Cancer, 2005, vol. 12 (2), pp. 245-262.
Yamamoto et al., "Phosphorylation of Axin, a Wnt Signal Negative Regulator, by Glycogen Synthase Kinase-3beta Regulates its Stability," The Journal of Biological Chemistry, 1999, vol. 274, No. 16, pp. 10681-10684.
Yamori et al., "Potent Antitumor Activity of MS-247, a Novel DNA Minor Groove Binder, Evaluated by an in Vitro and in Vivo Human Cancer Cell Line Panel," Cancer Research, 1999, vol. 59 (16), pp. 4042-4049.
Yanagawa et al., "Casein kinase I phosphorylates the Armadillo protein and induces its degradation in *Drosophila*," The EMBO Journal, 2002, vol. 21, No. 7, pp. 1733-1742.
Lemmon et al., "Cell Signaling by Receptor Tyrosine Kinases," Cell, 2010, vol. 141, pp. 1117-1134.
Extended European Search Report issued in corresponding European Patent Application No. 14756553.5 dated Nov. 2, 2016 (11 pages).
Choy et al., "High-Throughput Genotyping in Osteosarcoma Identifies Multiple Mutations in Phosphoinositide-3-Kinase and Other Oncogenes," Cancer, Jun. 1, 2012, vol. 118, pp. 2905-2914.
Joen et al., "Axin Inhibits Extracellular Signal-regulated Kinase Pathway by Ras Degradation via beta-Catenin," Journal of Biological Chemistry, May 11, 2007, vol. 282, No. 19, pp. 14482-14492 with Supplemental Material (4 pages).
Lovly et al., "Routine Multiplex Mutational Profiling of Melanomas Enables Enrollment in Genotype-Driven Therapeutic Trials," PLoS ONE, Apr. 2012, vol. 7, No. 4, e35309, pp. 1-9.
Communication pursuant to Article 94(3) EPC issued in corresponding European Patent Application No. 14756553.5 dated Aug. 23, 2017 (6 pages).
Garcia-Rostan et al., "Frequent Mutation and Nuclear Localization of B-Catenin in Anaplastic Thyroid Carcinoma," Cancer Research, vol. 59, pp. 1811-1815, Apr. 15, 1999.
Huang et al., "B-Catenin Mutations Are Frequent in Human Hepatocellular Carcinomas Associated with Hepatitis C Virus Infection," American Journal of Pathology, vol. 155, No. 6, pp. 1795-1801, Dec. 1999.
Legoix et al., "Beta-catenin mutations in hepatocellular carcinoma correlate with a low rate of loss of heterozygosity," Oncogene, vol. 18, No. 27, pp. 4044-4046, Jan. 1, 1999.
Choy et al., "High Throughput Genotyping in Osteosarcoma Identifies Multiple Mutations in PIK3CA and other Oncogenes," Cancer, vol. 118, No. 11, 2012, pp. 2905-2914.
Jeon et al., "Axin Inhibits Extracellular Signal-regulated Kinase Pathway by Ras Degradation via B-Catenin," The Journal of Biological Chemistry, vol. 282, No. 19, 2007, pp. 14482-14492.

\* cited by examiner

METHOD FOR PREDICTING RESPONSIVENESS TO COMPOUND INHIBITING MAPK SIGNAL TRANSDUCTION PATHWAY

The present application is a National Stage Application of PCT/JP2014/054846, filed Feb. 27, 2014, which claims priority from Japanese Patent Application No. 2013-036759, filed Feb. 27, 2013.

TECHNICAL FIELD

The present invention relates to a method of predicting responsiveness to a compound in cancer disease treatment which inhibits a mitogen-activated protein kinase (hereinafter abbreviated as MAPK) signaling pathway, a method of selecting a patient having responsiveness to the compound, and to a method of treating a cancer disease with the compound. More specifically, the present invention relates to a method of predicting responsiveness to a compound in cancer disease treatment which inhibits a MAPK signaling pathway, the method having a feature in measuring, using a biological sample derived from a cancer patient, whether or not β-catenin contained in the biological sample has at least one kind of mutation selected from the group consisting of (i) an active mutation and (ii) a substitution mutation of an asparagine residue to a serine residue at position 287, the method including determining a patient who is detected to have the mutation in β-catenin to have responsiveness to the compound that inhibits a MAPK signaling pathway. The present invention also relates to a reagent to be used in such prediction method. The present invention also relates to a method of selecting a patient to be subjected to cancer disease treatment with a compound that inhibits a MAPK signaling pathway, the method having the above-mentioned feature and including selecting a patient who is detected to have the mutation in β-catenin. The present invention also relates to a method of treating a cancer disease, the method having the above-mentioned feature and including administering a therapeutically effective amount of a compound that inhibits a MAPK signaling pathway to a patient who is detected to have the mutation in β-catenin.

BACKGROUND ART

A MAPK signaling pathway is a common signaling pathway involved in cell growth. The MAPK signaling pathway is a protein kinase cascade composed of three kinds of kinase groups, i.e., MAPK, MAPK kinase (hereinafter abbreviated as MAPKK), and MAPKK kinase (hereinafter abbreviated as MAPKKK), and is highly conserved in eukaryotes. In mammals, the MAPK are classified into four kinds of MAPK family molecules, specifically, extracellular signal-regulated protein kinases 1 and 2 (hereinafter referred to as ERK1/2), ERK5, Jun N-terminal kinase/stress-activated protein kinase (hereinafter abbreviated as JNK/SAPK), and p38 MAPK, and are known to form cascades independent of each other. Of those MAPK family molecules, ERK1/2 and ERK5 are each independently involved in a MAPK signaling pathway that is mainly activated by stimulation with a growth factor or the like. The MAPK signaling pathway in which ERK1/2 are involved is sometimes called a canonical MAPK signaling pathway. On the other hand, JNK/SAPK and p38 MAPK are each independently involved in a novel MAPK signaling pathway that is activated by an inflammatory cytokine such as interleukin-1 (IL-1) or tumor necrosis factor-α (TNF-α), or a physicochemical stress such as irradiation with UV light or hypertonic stimulation.

In the canonical MAPK signaling pathway, cell growth and survival are promoted by phosphorylation of downstream proteins by three kinds of kinases, i.e., Raf, MAPK/ERK kinase (hereinafter abbreviated as MEK), and ERK (Non Patent Document 1). Raf is a MAPKKK having serine/threonine kinase activity, and its family includes B-Raf (hereinafter sometimes referred to as BRAF), Raf-1, A-Raf, and the like. Raf is activated by Ras and operates the MAPK signaling pathway. MEK is a MAPKK having functions of phosphorylating not only a tyrosine residue but also a serine residue and a threonine residue, and is activated by phosphorylation by Raf and specifically phosphorylates ERK1/2. ERK is a MAPK having serine/threonine kinase activity. It is known that ERK1 and ERK2 having extremely high homology are present. ERK1/2 are phosphorylated by MEK1 and MEK2 (hereinafter referred to as MEK1/2).

In the canonical MAPK signaling pathway, when a growth factor such as epidermal growth factor (hereinafter abbreviated as EGF) binds to a receptor having tyrosine kinase activity on a cell membrane, a receptor tyrosine kinase (hereinafter sometimes abbreviated as RTK) is dimerized and activated (Non Patent Document 2). When the RTK is autophosphorylated, an adaptor protein Grb2 binds thereto. Grb2, to which a guanine nucleotide exchange factor, son of sevenless (SOS), is bound, promotes a guanosine diphosphate/guanosine triphosphate (hereinafter abbreviated as GDP/GTP) exchange reaction of a G protein, Ras (there are known K-ras, H-ras, and N-ras) (Non Patent Document 3). Then, Ras is activated, which leads to activation of Raf serine/threonine kinase. Raf directly phosphorylates MEK1/2, and phosphorylated MEK1/2 phosphorylate ERK1/2. Finally, phosphorylated ERK1/2 enter the nucleus and activate transcription of Elk-1 or cyclin D1, resulting in cell growth.

There are many reports on mutations and overexpression of factors involved in the MAPK signaling pathway in tumor cells. The overexpression and mutations of the receptor tyrosine kinase such as EGF receptor (hereinafter abbreviated as EGFR) or Her2 have been reported, which result in abnormal activation of the MAPK signaling pathway leading to malignant transformation (Non Patent Documents 4 to 6). In particular, the overexpression and mutations of EGFR are found in 50% or more of human malignant tumors. An active mutation of Ras is found in 30% of all malignant tumors, and in particular, is found in 90% of pancreatic cancers and 50% of colorectal cancers (Non Patent Documents 7 to 9). Similarly, an active mutation of BRAF is found in 63% of malignant melanomas, 45% of thyroid cancers, and 36% of ovary cancers (Non Patent Documents 10 to 12). An active mutation of BRAF is caused by constitutive activation of a part having a catalytic action through its structural change due to a substitution of a valine residue to a glutamic acid residue (V600E) in an amino acid residue at position 600, which is an active part. As a result, a downstream factor is activated without stimulation with a growth factor or the like, and hence cells abnormally grow, leading to malignant transformation (Non Patent Document 13).

MEK is positioned downstream of Ras and Raf and has high substrate specificity, and ERK as its substrate is activated in many types of tumor cells. Therefore, an inhibitor that targets MEK has been developed for the purpose of suppressing cell growth (Non Patent Document 14).

The MEK inhibitor developed for the first time is PD098059 (Parke-Davis). This compound exhibited inhibitory activity on MEK with an IC50 value of about 10 µmol/L. Next, U0126 (formerly, DuPont Pharma) was developed. U0126 inhibited MEK1/2 with an IC50 value of from about 5 to 7 nmol/L. PD098059 and U0126 exhibited growth-suppressive activity in vitro, but was not subjected to a clinical trial (Non Patent Documents 15 and 16).

The MEK inhibitor PD184352 (CI-1040, Parke-Davis) was reported for the first time as exhibiting a growth-suppressing effect in vivo and was subjected to a clinical trial. This compound was improved in both selectivity and inhibitory activity as compared to PD098059, and inhibited MEK1 in a non-adenosine triphosphate (ATP)-competitive manner with an IC50 value of 17 nmol/L. Further, at a preclinical stage, cell growth inhibitory activities on colorectal cancer cells and malignant melanoma were confirmed (Non Patent Document 17). PD0325901 (Pfizer) and AZD6244 (AstraZeneca/Array BioPharma) were developed as analogous compounds of PD184352. PD0325901 inhibited MEK1/2 in a non-ATP-competitive manner with an IC50 value of about 1 nmol/L, and exhibited more potent growth-suppressive activity than PD184352 in vivo (Non Patent Document 18). In a clinical trial, an antitumor effect and a decrease in phosphorylation of ERK were found in a phase I clinical trial and a phase II clinical trial (Non Patent Documents 19 and 20). AZD6244 inhibits MEK in a non-ATP-competitive manner with an IC50 value of about 12 nmol/L (Non Patent Document 21). This compound exhibits an antitumor effect in a clinical trial and is under a clinical trial at present.

A MEK inhibitor SMK-17 (Daiichi Sankyo Company, Limited), which was developed directed toward potent MEK inhibitory activity and excellent pharmacokinetics, has been found to have MEK1/2-specific inhibitory activity and growth-suppressive activity (Non Patent Document 22 and Patent Document 1).

An another signaling pathway, a Wnt/β-catenin signaling pathway, is known to involve in organism's development, cell growth, and oncogenesis. In the Wnt/β-catenin signaling pathway under a state in which a ligand Wnt does not act, a cancer-suppressing protein adenomatous polyposis coli (APC), a scaffold protein Axin (Non Patent Documents 23 to 25), glycogen synthase kinase-3 (hereinafter abbreviated as GSK-3), and casein kinase 1 (abbreviated as CK1) form a complex with β-catenin (hereinafter sometimes abbreviated as β-cat), in which β-catenin is phosphorylated by GSK-3 (Non Patent Document 23 and Non Patent Document 26) or CK1 (Non Patent Documents 27 to 29). Phosphorylated β-catenin is degraded via a ubiquitin-proteasome pathway (Non Patent Documents 30 to 32), and hence β-catenin is suppressed to a low expression level. However, when Wnt binds to a complex of a transmembrane receptor Frizzled (hereinafter abbreviated as Fz) and its coupled receptor LRP (Fz/LRP complex), Dishevelled is phosphorylated and phosphorylation activity of GSK-3 is inhibited via Axin (Non Patent Documents 33 and 34). This inhibits the phosphorylation of β-catenin. As a result, β-catenin is stored in the cytoplasm without being degraded (Non Patent Document 35). After that, β-catenin enters the nucleus and forms a complex with a transcription factor T-cell factor (hereinafter abbreviated as TCF) (Non Patent Documents 36 and 37). Finally, transcriptional activation of a target gene such as c-myc, which is involved in cell growth, survival, and apoptosis, or cyclin D1, which promotes cell growth, is caused.

Mutations of APC and β-catenin in tumor cells, which are constituent factors of the Wnt/β-catenin signaling pathway, have been reported. These mutations are found in 90% of colorectal cancers (Non Patent Documents 38 and 39). The mutations of APC are, in most cases, mutations deficient in binding sites for Axin and β-catenin (Non Patent Document 40). This results in that a complex that phosphorylates β-catenin is not formed, and β-catenin enters the nucleus without being phosphorylated and constitutively activates the Wnt/β-catenin signaling pathway. Active mutations among the mutations of β-catenin are, in most cases, substitution mutations of amino acid residues of a phosphorylation site by GSK-3, for example, a serine residue at position 33 (S33), serine residue at position 37 (S37), and threonine residue at position 41 (T41) thereof, and an amino acid residue of a phosphorylation site by CK1, for example, a serine residue at position 45 (S45) thereof, to an amino acid residue not phosphorylated by GSK-3 or CK1. This results in that β-catenin having an active mutation enters the nucleus without being phosphorylated by the above-mentioned complex and constitutively activates the Wnt/β-catenin signaling pathway, resulting in canceration of cells (Non Patent Document 39).

CITATION LIST

Patent Documents

[Patent Document 1] WO 2004/083167
[Patent Document 2] WO 2000/037141
[Patent Document 3] WO 2002/006213
[Patent Document 4] WO 2003/077914
[Patent Document 5] WO 2007/014011
[Patent Document 6] WO 2007/044515
[Patent Document 7] WO 2006/011466
[Patent Document 8] WO 2007/091736
[Patent Document 9] WO 2005/121142
[Patent Document 10] WO 2006/045514
[Patent Document 11] WO 2010/059503
[Patent Document 12] WO 2007/096259

Non-Patent Documents

[Non-Patent Document 1] Johnson, G. L. and R. Lapadat, Mitogen-activated protein kinase pathways mediated by ERK, JNK, and p38 protein kinases. Science, 2002. 298(5600): p. 1911-2.
[Non-Patent Document 2] Boonstra, J., et al., The epidermal growth factor. Cell Biol Int, 1995. 19(5): p. 413-30.
[Non-Patent Document 3] Schlessinger, J., Cell signaling by receptor tyrosine kinases. Cell, 2000. 103(2): p. 211-25.
[Non-Patent Document 4] Lynch, T. J., et al., Activating mutations in the epidermal growth factor receptor underlying responsiveness of non-small-cell lung cancer to gefitinib. N Engl J Med, 2004. 350(21): p. 2129-39.
[Non-Patent Document 5] Stephens, P., et al., Lung cancer: intragenic ERBB2 kinase mutations in tumours. Nature, 2004. 431(7008): p. 525-6.
[Non-Patent Document 6] Hynes, N. E. and H. A. Lane, ERBB receptors and cancer: the complexity of targeted inhibitors. Nat Rev Cancer, 2005. 5(5): p. 341-54.
[Non-Patent Document 7] Malumbres, M. and M. Barbacid, RAS oncogenes: the first 30 years. Nat Rev Cancer, 2003. 3(6): p. 459-65.
[Non-Patent Document 8] Downward, J., Targeting RAS signalling pathways in cancer therapy. Nat Rev Cancer, 2003. 3(1): p. 11-22.

[Non-Patent Document 9] Bos, J. L., et al., Prevalence of ras gene mutations in human colorectal cancers. Nature, 1987. 327(6120): p. 293-7.

[Non-Patent Document 10] Xing, M., BRAF mutation in thyroid cancer. Endocr Relat Cancer, 2005. 12(2): p. 245-62.

[Non-Patent Document 11] Sieben, N. L., et al., In ovarian neoplasms, BRAF, but not KRAS, mutations are restricted to low-grade serous tumours. J Pathol, 2004. 202(3): p. 336-40.

[Non-Patent Document 12] Brose, M. S., et al., BRAF and RAS mutations in human lung cancer and melanoma. Cancer Res, 2002. 62(23): p. 6997-7000.

[Non-Patent Document 13] Sumimoto, H., et al., Inhibition of growth and invasive ability of melanoma by inactivation of mutated BRAF with lentivirus-mediated RNA interference. Oncogene, 2004. 23(36): p. 6031-9.

[Non-Patent Document 14] Hoshino, R., et al., Constitutive activation of the 41-/43-kDa mitogen-activated protein kinase signaling pathway in human tumors. Oncogene, 1999. 18(3): p. 813-22.

[Non-Patent Document 15] Alessi, D. R., et al., PD 098059 is a specific inhibitor of the activation of mitogen-activated protein kinase in vitro and in vivo. J Biol Chem, 1995. 270(46): p. 27489-94.

[Non-Patent Document 16] Favata, M. F., et al., Identification of a novel inhibitor of mitogen-activated protein kinase. J Biol Chem, 1998. 273(29): p. 18623-32.

[Non-Patent Document 17] Friday, B. B. and A. A. Adjei, Advances in targeting the Ras/Raf/MEK/Erk mitogen-activated protein kinase cascade with MEK inhibitors for cancer therapy. Clin Cancer Res, 2008. 14(2): p. 342-6.

[Non-Patent Document 18] Sebolt-Leopold, J., The biological profile of PD 0325901: a second generation analog of CI-1040 with improved pharmaceutical potential. AACR Meeting Abstracts, 2004. 2004(925).

[Non-Patent Document 19] Lorusso, P., A phase 1-2 clinical study of a second generation oral MEK inhibitor, PD 0325901 in patients with advanced cancer. J Clin Oncol (Meeting Abstracts), 2005. 23(3066).

[Non-Patent Document 20] Wang, D., et al., Clinical experience of MEK inhibitors in cancer therapy. Biochim Biophys Acta, 2007. 1773(8): p. 1248-55.

[Non-Patent Document 21] Wallace, E., et al., Preclinical development of ARRY-142886, a potent and selective MEK inhibitor. Proc. Annu. Meet. Am. Assoc. Cancer Res., 2004. 45(A3891).

[Non-Patent Document 22] Kiga, M., et al., Antitumor effects of novel highly hydrophilic and non-ATP-competitive MEK1/2 inhibitor, SMK-17. Anticancer Drugs, 2012. 23(1): p. 119-30.

[Non-Patent Document 23] Hart, M. J., et al., Downregulation of beta-catenin by human Axin and its association with the APC tumor suppressor, beta-catenin and GSK3 beta. Curr Biol, 1998. 8(10): p. 573-81.

[Non-Patent Document 24] Kishida, S., et al., Axin, a negative regulator of the wnt signaling pathway, directly interacts with adenomatous polyposis coli and regulates the stabilization of beta-catenin. J Biol Chem, 1998. 273(18): p. 10823-6.

[Non-Patent Document 25] Ikeda, S., et al., Axin, a negative regulator of the Wnt signaling pathway, forms a complex with GSK-3beta and beta-catenin and promotes GSK-3beta-dependent phosphorylation of beta-catenin. EMBO J, 1998. 17(5): p. 1371-84.

[Non-Patent Document 26] Hinoi, T., et al., Complex formation of adenomatous polyposis coli gene product and axin facilitates glycogen synthase kinase-3 beta-dependent phosphorylation of beta-catenin and down-regulates beta-catenin. J Biol Chem, 2000. 275(44): p. 34399-406.

[Non-Patent Document 27] Amit, S., et al., Axin-mediated CKI phosphorylation of beta-catenin at Ser 45: a molecular switch for the Wnt pathway. Genes Dev, 2002. 16(9): p. 1066-76.

[Non-Patent Document 28] Liu, C., et al., Control of beta-catenin phosphorylation/degradation by a dual-kinase mechanism. Cell, 2002. 108(6): p. 837-47.

[Non-Patent Document 29] Yanagawa, S., et al., Casein kinase I phosphorylates the Armadillo protein and induces its degradation in *Drosophila*. EMBO J, 2002. 21(7): p. 1733-42.

[Non-Patent Document 30] Aberle, H., et al., beta-catenin is a target for the ubiquitin-protea some pathway. EMBO J, 1997. 16(13): p. 3797-804.

[Non-Patent Document 31] Latres, E., D. S. Chiaur, and M. Pagano, The human F box protein beta-Trcp associates with the Cul1/Skp1 complex and regulates the stability of beta-catenin. Oncogene, 1999. 18(4): p. 849-54.

[Non-Patent Document 32] Liu, C., et al., beta-Trcp couples beta-catenin phosphorylation-degradation and regulates *Xenopus* axis formation. Proc Natl Acad Sci USA, 1999. 96(11): p. 6273-8.

[Non-Patent Document 33] Cliffe, A., F. Hamada, and M. Bienz, A role of Dishevelled in relocating Axin to the plasma membrane during wingless signaling. Curr Biol, 2003. 13(11): p. 960-6.

[Non-Patent Document 34] Tamai, K., et al., A mechanism for Wnt coreceptor activation. Mol Cell, 2004. 13(1): p. 149-56.

[Non-Patent Document 35] Yamamoto, H., et al., Phosphorylation of axin, a Wnt signal negative regulator, by glycogen synthase kinase-3beta regulates its stability. J Biol Chem, 1999. 274(16): p. 10681-4.

[Non-Patent Document 36] Behrens, J., et al., Functional interaction of beta-catenin with the transcription factor LEF-1. Nature, 1996. 382(6592): p. 638-42.

[Non-Patent Document 37] Molenaar, M., et al., XTcf-3 transcription factor mediates beta-catenin-induced axis formation in *Xenopus* embryos. Cell, 1996. 86(3): p. 391-9.

[Non-Patent Document 38] Miyaki, M., et al., Characteristics of somatic mutation of the adenomatous polyposis coli gene in colorectal tumors. Cancer Res, 1994. 54(11): p. 3011-20.

[Non-Patent Document 39] Morin, P. J., et al., Activation of beta-catenin-Tcf signaling in colon cancer by mutations in beta-catenin or APC. Science, 1997. 275(5307): p. 1787-90.

[Non-Patent Document 40] Lamlum, H., et al., The type of somatic mutation at APC in familial adenomatous polyposis is determined by the site of the germline mutation: a new facet to Knudson's 'two-hit' hypothesis. Nat Med, 1999. 5(9): p. 1071-5.

[Non-Patent Document 41] Solit, D. B., et al., BRAF mutation predicts sensitivity to MEK inhibition. Nature, 2006. 439(7074): p. 358-62.

[Non-Patent Document 42] Dummer, R., et al., AZD6244 (ARRY-142886) vs temozolomide in patients with advanced melanoma: an open-label, randomized, multi-center, phase II study. J. Clin. Oncol., 2008. 26(9033).

[Non-Patent Document 43] Infante, J. R., et al., Safety and efficacy results from the first-in-human study of the oral MEK 1/2 inhibitor GSK1120212. J. Clin. Oncol., 2010. 28(2503).

[Non-Patent Document 44] Sebolt-Leopold, J. S., et al., Blockade of the MAP kinase pathway suppresses growth of colon tumors in vivo. Nat Med, 1999, 5(7): p. 810-6.

[Non-Patent Document 45] Takle, A. K., et al., The identification of potent and selective imidazole-based inhibitors of B-Raf kinase. Bioorg Med Chem Lett, 2006. 16(2): p. 378-81.

[Non-Patent Document 46] King, A. J., et al., Demonstration of a genetic therapeutic index for tumors expressing oncogenic BRAF by the kinase inhibitor SB-590885. Cancer Res, 2006. 66(23): p. 11100-5.

[Non-Patent Document 47] Kerr, J. F., History of the events leading to the formulation of the apoptosis concept. Toxicology, 2002. 181-182: p. 471-4.

[Non-Patent Document 48] Polakis, P., Wnt signal and cancer. Genes Dev, 2000. 14: p. 1837-51.

[Non-Patent Document 49] Published genetic information database http://www.sanger.ac.uk/

[Non-Patent Document 50] Ilyas, M., et al., beta-catenin mutations in cell lines established from human colorectal cancers. Proc Natl Acad Sci USA, 1999. 94: p. 10330-4.

[Non-Patent Document 51] Sunaga, N., et al., Constitutive Activation of the Wnt Signaling Pathway by CTNNBI (beta-Catenin) Mutations in a Subset of Human Lung Adenocarcinoma. Genes Chromosomes Cancer, 2001. 30: p. 316-21.

[Non-Patent Document 52] Price, S., Putative allosteric MEK1 and MEK2 inhibitors. Expert Opin Ther Patents, 2008. 18(6): p. 603-27.

[Non-Patent Document 53] Trujillo, J. I., MEK inhibitors: a patent review 2008-2010. Expert Opin Ther Patents, 2011. 21(7): p. 1045-69.

[Non-Patent Document 54] Sambrook J. et al. ed., Molecular Cloning: A Laboratory Manual (2d ed.) 1989 Cold Spring Harbor Laboratory Press, New York

[Non-Patent Document 55] Ulmer, K. M., Science, 1983. 219: p. 666-671

[Non-Patent Document 56] Ehrlich H. A. ed., PCR Technology. Principles and Applications for DNA Amplification. 1989 Stockton Press, New York

[Non-Patent Document 57] Kohler and Milstein, Nature, 1975 256: p. 495

[Non-Patent Document 58] Harlow & Lane, Antibodies, A Laboratory Manual,
1988 Cold Spring Harbor Press, New York

[Non-Patent Document 59] Goding, Monoclonal Antibodies, Principles and Practice (2d ed.) 1986 Academic Press, New York

[Non-Patent Document 60] Yamori, T., et al., Potent antitumor activity of MS-247, a novel DNA minor groove binder, evaluated by an in vitro and in vivo human cancer cell line panel. Cancer Res, 1999. 59(16): p. 4042-9.

[Non-Patent Document 61] Wilhelm, S., et al., Discovery and development of sorafenib: a multikinase inhibitor for treating cancer. Nat Rev Drug Discov, 2006. 5(10): p. 835-44.

SUMMARY OF INVENTION

Problem to be Solved by the Invention

In a therapeutic field of a cancer disease in recent years, development of a molecularly targeted drug has become mainstream, and a concept of selecting a patient who receives the effect of the drug with certainty and administrating the drug to the selected patient has been becoming established. Therefore, at the time of the development of the molecularly targeted drug, there is a demand for development of a method of evaluating a drug effect for the purpose of patient selection or side effect reduction.

For example, it has been reported that the MEK inhibitor can be considered to exhibit an antitumor effect on a malignant tumor having an active mutation of BRAF, which activates a MEK, and hence sensitivity of the malignant tumor to the MEK inhibitor can be predicted by detecting a BRAF V600E mutation as the active mutation (Non Patent Document 41). However, clinical responses to MEK inhibitors PD0325901 and AZD6244 of patients with malignant melanoma having an active BRAF mutation in a clinical trial are about 10% and 11% in terms of a total of a partial response and a complete response, respectively, and thus a high effect has not been obtained (Non Patent Documents 42 and 43).

An object of the present invention is to provide a method of predicting sensitivity to a molecularly targeted drug, and a method of selecting a patient who is determined to have high responsiveness to the drug, in order to enable effective treatment of a cancer disease with a molecularly targeted drug.

Means for Solving the Object

The inventors of the present invention have made extensive investigations in order to achieve the above-mentioned object, and have found that each of MEK inhibitors SMK-17 (Non Patent Document 22 and Patent Document 1) and PD184352 (Non Patent Document 44), and a BRAF-selective inhibitor SB590885 (Non Patent Documents 45 and 46) induces apoptosis selectively in cells having an active β-catenin mutation. In addition, the inventors have found that apoptosis induction by SMK-17 was not observed in cells in which a function of a Wnt/β-catenin signaling pathway was lost by knockdown of β-catenin gene or forced expression of DN-TCF4, and that apoptosis was induced by SMK-17 in cells in which a function of a Wnt/β-catenin signaling pathway was activated by forced expression of active β-catenin or wnt3a stimulation. Further, the inventors have found that SMK-17 exhibits a tumor regression effect on a tumor having an active β-catenin mutation in vivo. Thus, the present invention has been accomplished by clarifying a relationship between the apoptosis induction of tumor cells by the inhibition of the MAPK signaling pathway and its tumor regression effect, and the activation of the Wnt/β-catenin signaling pathway.

That is, the present invention relates to the following.
1. A method of selecting a patient to be subjected to cancer disease treatment with a compound that inhibits a MAPK signaling pathway, the method including:
    using a biological sample derived from a cancer patient, measuring whether or not β-catenin contained in the biological sample has at least one kind of mutation selected from the group consisting of (i) an active mutation and (ii) a substitution mutation of an asparagine residue to a serine residue at position 287; and
    selecting a patient who is detected to have the mutation in β-catenin as a patient to be subjected to cancer disease treatment with a compound that inhibits a MAPK signaling pathway.
2. A method of predicting responsiveness to cancer disease treatment with a compound that inhibits a MAPK signaling pathway, the method including:
    using a biological sample derived from a cancer patient, measuring whether or not β-catenin contained in the biological sample has at least one kind of mutation selected from the group consisting of (i) an active mutation and (ii) a substitution mutation of an asparagine residue to a serine residue at position 287; and determining a patient who is detected to have the mutation in β-catenin to have responsiveness to cancer disease treatment with a compound that inhibits a MAPK signaling pathway.

3. The method according to the above-mentioned item 2., in which the responsiveness to cancer disease treatment with a compound that inhibits a MAPK signaling pathway is cancer regression due to apoptosis induction in the cancer disease treatment with the compound.

4. A method of treating a cancer disease, the method including:

using a biological sample derived from a cancer patient, measuring whether or not β-catenin contained in the biological sample has at least one kind of mutation selected from the group consisting of (i) an active mutation and (ii) a substitution mutation of an asparagine residue to a serine residue at position 287;

selecting a patient who is detected to have the mutation in β-catenin as a patient to be subjected to cancer disease treatment with a compound that inhibits a MAPK signaling pathway; and administering a therapeutically effective amount of the compound that inhibits a MAPK signaling pathway to the selected patient.

5. The method according to any one of the above-mentioned items 1. to 4., in which the active mutation is at least one mutation selected from the following:
(1) a substitution mutation of a serine residue at position 33, a serine residue at position 37, a threonine residue at position 41, or a serine residue at position 45 in an amino acid sequence of β-catenin, which is a substitution mutation to an amino acid residue other than a serine residue or a threonine residue; and
(2) a deletion mutation of a serine residue at position 33, a serine residue at position 37, a threonine residue at position 41, or a serine residue at position 45 in an amino acid sequence of β-catenin.

6. The method according to any one of the above-mentioned items 1. to 4., in which the active mutation is at least one mutation selected from the following:
(3) a substitution mutation of a serine residue at position 33 or a serine residue at position 45 in an amino acid sequence of β-catenin, which is a substitution mutation to an amino acid residue other than a serine residue or a threonine residue; and
(4) a deletion mutation of a serine residue at position 45 in an amino acid sequence of β-catenin.

7. The method according to any one of the above-mentioned items 1. to 6., in which the biological sample is a biological sample containing a cancer cell or a cancer tissue.

8. The method according to any one of the above-mentioned items 1. to 7., in which the compound that inhibits a MAPK signaling pathway is at least one compound selected from the group consisting of a compound that inhibits a MAPKKK, a compound that inhibits a MAPKK, and a compound that inhibits a MAPK.

9. The method according to the above-mentioned item 8., in which the at least one compound selected from the group consisting of a compound that inhibits a MAPKKK, a compound that inhibits a MAPKK, and a compound that inhibits a MAPK is at least one compound selected from the group consisting of a compound that inhibits B-Raf and a compound that inhibits MEK1/2.

10. A reagent for detecting a presence or absence of the mutation of β-catenin in the method of any one of the above-mentioned items 1. to 9., the reagent including as an active ingredient a molecule as described in any one of the following (a) to (d):
(a) an oligonucleotide primer that specifically binds to a nucleic acid comprising a consecutive partial nucleotide sequence containing a mutation site of a gene encoding β-catenin having the mutation;
(b) an oligonucleotide primer set consisting of: an oligonucleotide primer that specifically binds to part of a complementary sequence to a nucleotide sequence in a 5'-side region of a mutation site of a gene encoding β-catenin having the mutation; and an oligonucleotide primer that specifically binds to part of a nucleotide sequence in a 3'-side region of a mutation site of a β-catenin gene having the mutation;
(c) an oligonucleotide probe that specifically binds to a nucleic acid consisting of a consecutive partial nucleotide sequence containing a mutation site of a gene encoding β-catenin having the mutation; and
(d) an antibody that specifically binds to β-catenin having said mutation.

11. The reagent according to the above-mentioned item 10., in which: the molecule as the active ingredient is the oligonucleotide primer as described in the (a), the oligonucleotide primer set as described in the (b), or the oligonucleotide probe as described in the (c); and the mutation is any one of mutations selected from the following:
(A) a substitution mutation of a serine residue at position 33, a serine residue at position 37, a threonine residue at position 41, or a serine residue at position 45 in an amino acid sequence of β-catenin, which is a substitution mutation to an amino acid residue other than a serine residue or a threonine residue;
(B) a deletion mutation of a serine residue at position 33, a serine residue at position 37, a threonine residue at position 41, or a serine residue at position 45 in an amino acid sequence of β-catenin; and
(C) a substitution mutation of an asparagine residue to a serine residue at position 287 in an amino acid sequence of β-catenin.

12. The reagent according to the above-mentioned item 10., in which: the molecule as the active ingredient is the oligonucleotide primer as described in the (a), the oligonucleotide primer set as described in the (b), or the oligonucleotide probe as described in the (c); and the mutation site of a gene encoding β-catenin having the mutation is a mutation at position 98, position 109, position 110, position 121, position 133, position 134, or position 860 in a nucleotide sequence set forth in SEQ ID NO: 1 of a sequence listing.

13. The reagent according to the above-mentioned item 10., in which: the molecule as the active ingredient is the oligonucleotide primer as described in the (a), the oligonucleotide primer set as described in the (b), or the oligonucleotide probe as described in the (c); and the mutation site of a gene encoding β-catenin having the mutation and a mutation at the mutation site is: a mutation of cytosine to adenine at position 98, a mutation of thymine to cytosine at position 109, a mutation of cytosine to thymine at position 110, a mutation of adenine to guanine at position 121, a mutation of thymine to cytosine at position 133, a mutation of cytosine to thymine at position 134, or a mutation of adenine to guanine at position 860 in a nucleotide sequence set forth in SEQ ID NO: 1 of a sequence listing.

14. The reagent according to the above-mentioned item 10., in which: the molecule as the active ingredient is the antibody as described in the (d); and the mutation includes any one of mutations selected from the following:
   (A) a substitution mutation of a serine residue at position 33, a serine residue at position 37, a threonine residue at position 41, or a serine residue at position 45 in an amino acid sequence of β-catenin, which is a substitution mutation to an amino acid residue other than a serine residue or a threonine residue;
   (B) a deletion mutation of a serine residue at position 33, a serine residue at position 37, a threonine residue at position 41, or a serine residue at position 45 in an amino acid sequence of β-catenin; and
   (C) a substitution mutation of an asparagine residue to a serine residue at position 287 in an amino acid sequence of β-catenin.

Advantage of the Invention

According to the present invention, the method of predicting responsiveness to cancer disease treatment with a compound that inhibits a MAPK signaling pathway can be provided, the method including using a biological sample derived from a cancer patient, measuring whether or not β-catenin contained in the biological sample has at least one kind of mutation selected from the group consisting of (i) an active mutation and (ii) a substitution mutation of an asparagine residue to a serine residue at position 287; the method of selecting a patient to be subjected to cancer disease treatment with a compound that inhibits a MAPK signaling pathway; and the method of treating a cancer disease, the method including administering the compound to the patient selected by the above-mentioned method.

The method according to the present invention allows evaluation of the effect of a drug containing a compound that inhibits a MAPK signaling pathway in a cancer patient before administration of the drug. In addition, the method according to the present invention allows selection of a patient who is determined to have high responsiveness to the drug, and allows an effective treatment of a cancer disease with the drug. Further, the method according to the present invention can be performed in vitro by using a biological sample derived from a cancer patient, and hence impose less burden on a patient. As described above, the method according to the present invention is useful in the therapeutic field of a cancer disease.

BRIEF DESCRIPTION OF DRAWINGS

In FIG. 7, "ABC" represents active beta-catenin (active β-catenin). The panel A shows that TCF4 transcriptional activity was increased in the cells with forced expression of active β-catenin. The panel B shows that the number of sub-G1 cells was significantly increased in the cells with forced expression of active β-catenin as compared to the control cells (Example 5).

In FIG. 9, "β-cat wt" represents wild-type β-catenin, and "R-cat mutation" represents an active β-catenin mutation. The apoptosis-positive cells are detected by a TUNEL assay, and the number of thereof is represented as the number of TUNEL-positive cells per field (TUNEL positive/field) (Example 6).

DETAILED DESCRIPTION OF THE INVENTION

Figure 1:
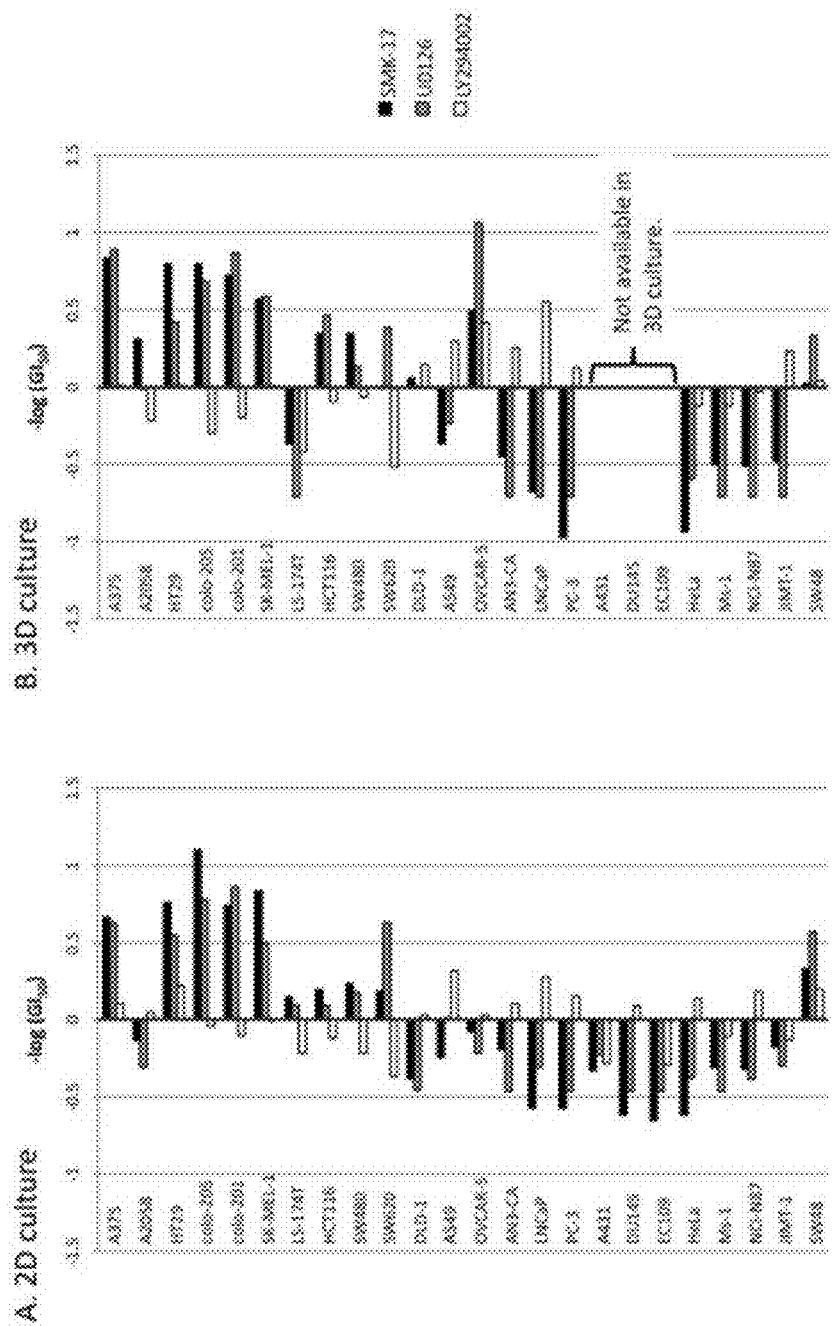
FIG. 1 shows the results of studies on the tumor cell growth-suppressive activity of MEK inhibitors SMK-17 and U0126. Active β-catenin mutant cell lines SW48, colo-205, colo-201, SK-MEL-1, and HCT_116 each exhibited high sensitivity to SMK-17 and U0126. These cells had low sensitivity to a PI3K inhibitor LY294002. The panel A and the panel B show the results of studies in two-dimensional culture (2D culture) and three-dimensional culture (3D culture), respectively (Example 1).

The present invention relates to a method of predicting responsiveness to cancer disease treatment with a compound that inhibits a MAPK signaling pathway, the method having a feature in that a mutation of β-catenin contained in a biological sample derived from a cancer patient is detected as a sensitivity factor for a compound that inhibits a MAPK signaling pathway. The present invention also relates to a method of selecting a patient having responsiveness to a compound that inhibits a MAPK signaling pathway, the method having the above-mentioned feature. The present invention also relates to a method of treating a cancer disease, the method including administering the compound that inhibits a MAPK signaling pathway to the patient selected by the above-mentioned method.

Herein, the "responsiveness to cancer disease treatment with a compound that inhibits a MAPK signaling pathway" refers to sensitivity or reactivity to a compound that inhibits a MAPK signaling pathway, and more specifically, means apoptosis induction and cancer regression resulting therefrom in cancer disease treatment with the compound.

Herein, the "apoptosis" refers to a collective term for programmed cell deaths (Non Patent Document 47). The apoptosis refers to controlled and regulated cell deaths, which cells constituting a body of a multicellular organism positively causes to keep an individual in a better state. It is known as a feature of the apoptosis that nuclear condensation and the subsequent DNA fragmentation occur after the change of a cell membrane structure, and cells are degraded into a small sized-structure referred to as "apoptotic body". DNA content of the apoptotic body is less as compared to those of normal cells and growing cells. Therefore, the apoptosis may be detected by measuring DNA content of cells to detect the apoptotic body. The apoptotic body formation is detected as sub-G1 phase in the measurement of a cell cycle. The cell cycle may be measured, for example, by a well-known method utilizing a flow cytometer.

The "cancer" generally means a malignant tumor in a narrow sense, and refers to a malignant tumor of an epithelial cell origin. On the other hand, a non-epithelial malignant tumor is called sarcoma. The "malignant tumor" refers to particularly a histological tumor having a high infiltration property and exhibiting malignancy such as growth and metastasis, wherein the histological tumor is formed by autonomous and excessive growth of a tissue or cells contrary to in vivo control. According to the histopathological classification, the cancer may be classified into three kinds, i.e., adenocarcinoma, squamous cell carcinoma, and transitional cell carcinoma. The adenocarcinoma is a cancer derived from glandular tissue, and examples thereof may include colorectal cancer, breast cancer, stomach cancer, lung cancer, gallbladder cancer, kidney cancer, prostate cancer, duodenum cancer, pancreatic cancer, ovary cancer, uterus cervix cancer, and uterus corpus cancer. The squamous cell carcinoma is a tumor formed by growth of malignantly transformed epithelial basal cells with increased atypia and polymorphia in a subepithelial connective tissue, and examples thereof may include oral cancer, tongue cancer, pharyngeal cancer, esophagus cancer, bronchus cancer, and laryngeal cancer. The transitional cell carcinoma is a cancer derived from a transitional epithelial tissue, and examples thereof may include bladder cancer, renal pelvis cancer, ureter cancer, and oral cancer. Meanwhile, examples of the sarcoma include fibrosarcoma, myxosarcoma, liposarcoma, chondrosarcoma, osteosarcoma, rhabdomyoma, leiomyosarcoma, angiosarcoma, and malignant lymphoma.

A frequency of the sarcoma in the malignant tumor is low. Therefore, the term "cancer" is often used in the same meaning as the "malignant tumor". Herein, the "cancer" and the "malignant tumor" are exchangeably used as synonyms.

The method of predicting responsiveness to cancer disease treatment with a compound that inhibits a MAPK signaling pathway according to the present invention includes: using a biological sample derived from a cancer patient, measuring whether or not β-catenin contained in the biological sample has a mutation; and determining a patient who is detected to have the mutation in β-catenin to have responsiveness to cancer disease treatment with a compound that inhibits a MAPK signaling pathway.

The method of selecting a patient having responsiveness to a compound that inhibits a MAPK signaling pathway according to the present invention includes: using a biological sample derived from a cancer patient, measuring whether or not β-catenin contained in the biological sample has a mutation; and selecting a patient who is detected to have the mutation in β-catenin as a patient to be subjected to cancer disease treatment with a compound that inhibits a MAPK signaling pathway.

The method of treating a cancer disease with a compound that inhibits a MAPK signaling pathway according to the present invention includes: using a biological sample derived from a cancer patient, measuring whether or not β-catenin contained in the biological sample has a mutation; selecting a patient who is detected to have the mutation in β-catenin as a patient to be subjected to cancer disease treatment with a compound that inhibits a MAPK signaling pathway; and administering a therapeutically effective amount of the compound that inhibits a MAPK signaling pathway to the selected patient.

The β-catenin mutation to be detected as the sensitivity factor for the compound that inhibits a MAPK signaling pathway is (i) an active mutation and (ii) a substitution mutation of an asparagine residue to a serine residue at position 287 in the amino acid sequence of β-catenin. When at least one kind of mutation selected from the group consisting of (i) an active mutation and (ii) a substitution mutation of an asparagine residue to a serine residue at position 287 in the amino acid sequence of β-catenin is detected in the biological sample derived from a cancer patient, the cancer patient is determined to have responsiveness to the compound that inhibits a MAPK signaling pathway, or the cancer patient is selected as a patient to be subjected to cancer disease treatment with the compound that inhibits a MAPK signaling pathway. Alternatively, when at least one kind of mutation selected from the group consisting of (i) an active mutation and (ii) a substitution mutation of an asparagine residue to a serine residue at position 287 in the amino acid sequence of β-catenin is detected in the biological sample derived from a cancer patient, a therapeutically effective amount of the compound that inhibits a MAPK signaling pathway is administered to the cancer patient.

Herein, the "active mutation of β-catenin" refers to a mutation that brings about a state in which β-catenin constitutively functions in cells, that is, a mutation that brings about a state in which the Wnt/β-catenin signaling pathway is constitutively activated. An example of the active mutation of β-catenin may be a mutation of an amino acid residue at a phosphorylation site by a serine/threonine protein kinase GSK-3 or CK1. β-catenin having such active mutation enters the nucleus without being phosphorylated, and constitutively activates the Wnt/β-catenin signaling pathway, resulting in the canceration of cells (Non Patent Document 39). Examples of the amino acid residue at the phosphorylation site by GSK-3 or CK1 may include serine residues or threonine residues at position 33, position 37, position 41, and position 45 in the amino acid sequence of β-catenin. Examples of the mutation of the amino acid residue at the phosphorylation site by GSK-3 may include substitution mutations of a serine residue at position 33 (S33), a serine residue at position 37 (S37), and a threonine residue at position 41 (T41) in the amino acid sequence of β-catenin to an amino acid residue not phosphorylated by GSK-3, i.e., an amino acid residue other than a serine residue or a threonine residue. An example of the mutation of the amino acid residue at the phosphorylation site by CK1 may be a substitution mutation of a serine residue at position 45 (S45) in the amino acid sequence of β-catenin to an amino acid residue not phosphorylated by CK1, i.e. an amino acid residue other than a serine residue and a threonine residue. In addition, examples of the active mutation of β-catenin may include a deletion of an amino acid residue at the phosphorylation site by GSK-3 or CK1, and an insertion of an amino acid into the site.

The active mutation of β-catenin has been reported in many kinds of cancer diseases. For example, any one kind or two or more kinds of substitution mutations of S33, S37, T41, and S45 of β-catenin have been found in cololectal cancer, sporadic corpus uteri cancer, desmoid tumor, hepatocellular carcinoma, hepatoblastoma, nephroblastoma (Wilms' tumor), sporadic medulloblastoma, ovarian endometrioid carcinoma, prostate cancer, and thyroid cancer (Non Patent Document 48).

The active mutation of β-catenin has also been reported in a number of malignant tumor lines. For example, there is a report on a substitution of T41 of β-catenin to alanine, and there are also reports on substitutions of S33 to cysteine, phenylalanine, and tyrosine, and substitutions of S37 and S45 to phenylalanine and proline (Non Patent Document 49).

The nucleotide sequence of a coding region of wild-type β-catenin gene is set forth in SEQ ID NO: 1 of the sequence listing. In addition, the amino acid sequence of wild-type β-catenin is set forth in SEQ ID NO: 2. Herein, when the position of a certain nucleotide in the nucleotide sequence of β-catenin gene is mentioned, the position is expressed as a position in the nucleotide sequence set forth in SEQ ID NO: 1. Herein, when the position of a certain amino acid residue in the amino acid sequence of β-catenin is mentioned, the position is expressed as a position in the amino acid sequence set forth in SEQ ID NO: 2.

Herein, a one-letter abbreviation is used in representing a mutation in an amino acid sequence, and an amino acid substitution of an amino acid residue X to an amino acid residue Z at position y in an amino acid sequence is sometimes expressed as XyZ. For example, an amino acid substitution of a serine residue to a tyrosine residue at position 33 is expressed as S33Y. In addition, a deletion of an amino acid residue X at position y is expressed as Xydel. For example, a deletion of a serine residue at position 45 is expressed as S45del.

In addition, herein, in the case of representing a mutation in a nucleotide sequence, the first nucleotide of a start codon in the nucleotide sequence is defined as position 1, and a substitution mutation of a base N to a base M at position n is sometimes expressed as nN>M. For example, a substitution mutation of cytosine to adenine at position 98 is expressed as 98C>A.

Table 1 shows examples of the active mutation and N287S mutation of β-catenin detected in malignant tumor lines.

TABLE 1

| Type of tumor cell line | Name of tumor cell line | β-Catenin Amino acid mutation | Gene mutation |
| --- | --- | --- | --- |
| Colorectal cancer | SW48 | S33Y | 98C > A |
| | HCT_116 | S45del | In-frame deletion of three-nucleotides |
| | LS174-T | S45F | 134C > T |
| | Colo201 | N287S | 860A > G |
| | Colo205 | N287S | 860A > G |
| Skin cancer | SK-MEL-1 | S33C | 98C > G |
| Lung cancer | SW1573 | S33F | 98C > T |
| | A427 | T41A | 121A > G |
| Duodenum cancer | HUTU-80 | S37F | 100C > T |
| hCG-producing ovary adenocarcinoma | RTSG | S37P | 109T > C |
| Adrenal cortex cancer | NCI-H295 | S45P | 133T > C |

As the active mutation of β-catenin, mutations of S33Y, S45del, and S45F have been reported in colorectal cancer cell lines, SW48 cells, HCT_116 cells, and LS-174T cells, respectively. In addition, a mutation of S33C has been reported in a skin cancer cell line, SK-MEL-1 cells. As shown in Examples described later, these cell lines exhibited high responsiveness to treatment with a MEK inhibitor or BRAF inhibitor, which was a compound that inhibited a MAPK signaling pathway, as compared to cells having wild-type β-catenin, and apoptosis thereof was induced.

In addition to the foregoing, there are reports on the active mutation of β-catenin, which is a mutation such as: S33F and T41A in lung cancer cell lines, SW1573 cells and A427 cells, respectively; S37F in a duodenum cancer cell line, HUTU-80 cells; S37P in a hCG-producing ovary adenocarcinoma cell line, RTSG cells; and S45P in an adrenal cortex cancer cell line, NCI-H295 cells (Non Patent Documents 50 and 51).

On the other hand, it has not been reported that a substitution mutation of an asparagine residue to a serine residue at position 287 (N287S) is an active mutation of β-catenin. However, as shown in Examples described later, apoptosis was induced by MEK inhibitor treatment in colorectal cancer cell lines having the above-mentioned substitution mutation, colo201 cells and colo205cells (Non Patent Document 51), as with cells having active mutations of β-catenin. This fact indicates that the N287S mutation may be utilized as a sensitivity factor for the compound that inhibits a MAPK signaling pathway.

The β-catenin mutation that may be utilized as the sensitivity factor for the compound that inhibits a MAPK signaling pathway in the method according to the present invention is preferably one or more mutations selected from the following:

(1) a substitution mutation of a serine residue at position 33, a serine residue at position 37, a threonine residue at position 41, or a serine residue at position 45 to an amino acid residue other than a serine residue or a threonine residue;

(2) a deletion mutation of a serine residue at position 33, a serine residue at position 37, a threonine residue at position 41, or a serine residue at position 45; and (3) a substitution mutation of an asparagine residue to a serine residue at position 287.

The β-catenin mutation that may be utilized as the sensitivity factor for the compound that inhibits a MAPK signaling pathway in the method according to the present invention is more preferably one or more mutations selected from the following:

(4) a substitution mutation of a serine residue at position 33 or a serine residue at position 45 to an amino acid residue other than a serine residue or a threonine residue;

(5) a deletion mutation of a serine residue at position 45; and (6) a substitution mutation of an asparagine residue to a serine residue at position 287.

The detection of the mutation of β-catenin may be performed by detecting a mutation of β-catenin gene. The detection of the mutation of β-catenin gene is preferably performed by detecting the presence or absence of a missense mutation for codons encoding any one kind or two or more kinds of amino acid residues at position 33, position 37, position 41, position 45, and position 287 in the amino acid sequence of β-catenin. The "missense mutation" means a single base pair substitution that changes a genetic code so as to dispose an amino acid different from a normal amino acid at a site of interest. When a difference in nucleotide is detected in a comparison between the nucleotide sequence of β-catenin gene in a test sample and the nucleotide sequence (SEQ ID NO: 1) of wild-type β-catenin gene, the β-catenin gene in the test sample can be determined to have a mutation.

More preferred examples of the mutation of β-catenin gene may include mutations of cytosine at position 98, thymine at position 109, cytosine at position 110, adenine at position 121, thymine at position 133, cytosine at position 134, and adenine at position 860 in the β-catenin gene, and even more preferred examples may include gene mutations shown in Table 1.

The detection of the mutation of β-catenin gene may be performed by using a method known per se. For example, a nucleic acid of a full-length or fragment including a mutation site to be detected of the gene is amplified and a nucleotide sequence of the amplified nucleic acid is determined by a well-known technology. The amplification of the nucleic acid may be performed by a nucleic acid amplification method known per se, such as a polymerase chain reaction (abbreviated as PCR). A nucleotide sequence of the resultant amplified product is determined, for example, by a DNA sequencing method such as a direct sequencing method. Such mutation detection method may be performed with reference to methods described in the documents (e.g., Non Patent Documents 50 and 51). As a sequence determination method, there may be utilized a hybridization method, a restriction enzyme fragment length polymorphism (RFLP) analysis method, and the like in addition to the sequencing method. When β-catenin gene amplified from a test sample is not identical to a wild-type one, the β-catenin gene in the test sample can be determined to have a mutation. In addition, a known single nucleotide mutation analysis method may be utilized. For example, when the PCR is performed, the detection of the mutation of β-catenin gene may be performed by using a primer consisting of a complementary nucleotide sequence to a consecutive partial nucleotide sequence containing a mutation site as a primer, to detect the presence or absence of an amplified product. When the β-catenin gene in the test sample is amplified using such primer, the β-catenin gene in the test sample can be determined to have a mutation of interest. When the β-catenin gene in the test sample is not amplified, the β-catenin gene in the test sample can be determined to have no mutation capable of being detected with the primer. In the hybridization method, a nucleic acid of a gene to be detected is amplified, a hybridization probe is brought into contact with the nucleic acid, and the presence or absence of hybridization between the hybridization probe and the nucleic acid is detected. The "hybridization probe" refers to a polynucleotide that can distinguish between two kinds of nucleic acids in a detectable manner. As the hybridization probe, a nucleic acid fragment having a complementary nucleotide sequence to a nucleotide sequence of a region containing a mutation to be detected is used. The detection of the hybridization may be performed by a well-known technology. When the probe hybridizes with the nucleic acid of the β-catenin gene in the test sample, the β-catenin gene in the test sample can be determined to have a mutation.

The detection of the mutation of β-catenin may also be performed by detecting a mutation of an amino acid thereof. The mutation of the amino acid of β-catenin may be detected by an immunological technique using an antibody specifically binding to a β-catenin mutant. The antibody specifically binding to a β-catenin mutant means an antibody more selectively binding to a β-catenin mutant to be detected as compared to a β-catenin mutant other than the β-catenin mutant to be detected, wild-type β-catenin, and a protein other than β-catenin. Examples of the immunological technique include a radioimmunoassay method (RIA method), an enzyme-linked immunosorbent assay method (ELISA method), western blotting, immunohistological staining, and flow cytometry analysis. A desired antibody may be produced by the existing general production method using as an immunogen an oligopeptide comprising a β-catenin mutant, preferably a partial amino acid sequence of a β-catenin mutant which corresponds to a partial region containing an amino acid residue at the position where the mutation is present. Alternatively, a desired commercially available antibody may also be used.

The detection of the mutation, in particular, active mutation of β-catenin may also be performed by detecting a reaction that is caused by the activation of the Wnt/β-catenin signaling pathway, for example, the enhancement of TCF transcriptional activity or the intranuclear accumulation of β-catenin, because the active mutation activates the signaling pathway. A method of detecting the TCF transcriptional activity is known per se and may be performed, for example, by a TOPFLASH reporter assay used in Examples described later. A method of detecting the intranuclear accumulation of β-catenin may be performed by a well-known technology relating to the detection of an intranuclear protein, for example, an evaluation method based on immunostaining. When an increase in TCF transcriptional activity or the intranuclear accumulation of β-catenin is observed in a test sample, β-catenin in the test sample can be determined to have an active mutation.

Herein, the "biological sample" refers to a tissue, a fluid, and cells isolated from an individual and a mixture thereof. Examples thereof may include, but not limited to, a tumor biopsy, cerebrospinal fluid, pleural fluid, intraperitoneal fluid, lymph fluid, a skin section, blood, urine, feces, phlegm, a respiratory organ, an intestinal tract, a genitourinary tract, saliva, milk, and a digestive organ, and cells collected therefrom. The "biological sample" is preferably a sample containing cancer cells, and is more preferably exemplified by a tissue or cells obtained by excision or biopsy, or cells derived from pleural fluid or intraperitoneal fluid. The biological sample is still more preferably a sample containing cancer cells or a cancer tissue.

Herein, the "compound that inhibits a MAPK signaling pathway" refers to a compound that reduces a function of the MAPK signaling pathway. The compound that inhibits a MAPK signaling pathway encompasses a compound that reduces a function of a constituent element such as a protein constituting the MAPK signaling pathway, and a compound that reduces a function of the MAPK signaling pathway, for example, a function of promoting the survival and growth of cells. In this connection, a compound that reduces a function of a target on which the compound acts is sometimes referred to as "inhibitor".

The MAPK signaling pathway is classified into one activated by stimulation with a growth factor or the like, and one activated by an inflammatory cytokine or a physico-chemical stress. Herein, the "compound that inhibits a MAPK signaling pathway" is preferably a "compound that inhibits a canonical MAPK signaling pathway" that is activated by stimulation with a growth factor or the like.

The compound that inhibits a MAPK signaling pathway is preferably a compound that inhibits the pathway upstream of MEK in the signaling pathway, and may be at least one compound selected from the group consisting of a compound that inhibits a MAPKKK, a compound that inhibits a MAPKK, and a compound that inhibits a MAPK. The compound that inhibits a MAPKKK is preferably a compound that inhibits Raf, more preferably a compound that inhibits BRAF. The compound that inhibits a MAPKK is preferably a compound that inhibits a MEK, more preferably a compound that inhibits MEK1/2. The compound that inhibits a MAPK is preferably a compound that inhibits an ERK, more preferably a compound that inhibits ERK1/2. That is, the compound that inhibits a MAPK signaling pathway is more preferably at least one compound selected from the group consisting of a compound that inhibits BRAF and a compound that inhibits MEK1/2, still more preferably a compound that inhibits MEK1/2.

Examples of the compound that inhibits a MEK may include a compound disclosed in WO 2000/037141 (Patent Document 2) (such as PD-184352), a compound disclosed in WO 2002/006213 (Patent Document 3) (such as PD-0325901), a compound disclosed in WO 2003/077914 (Patent Document 4) (such as selumetinib), a compound disclosed in WO 2007/014011 (Patent Document 5) (such as refametinib), a compound disclosed in WO 2007/044515 (Patent Document 6) (such as GDC-0973, i.e., XL-518), a compound disclosed in WO 2006/011466 (Patent Document 7) (such as RO-4987655), a compound disclosed in WO 2007/091736 A1 (Patent Document 8) (such as RO-5126766), a compound disclosed in WO 2005/121142 (Patent Document 9) (such as GSK-1120212, i.e., trametinib), a compound disclosed in WO 2006/045514 (Patent Document 10) (such as AS-703026), a compound disclosed in WO 2010/059503 (Patent Document 11) (such as TAK-733), a compound disclosed in WO 2007/096259 (Patent Document 12) (such as RO-5068760), a compound disclosed in Expert Opin Ther Patents, 2008. 18(6): p. 603-27. (Non Patent Document 52), and a compound disclosed in Expert Opin Ther Patents, 2011. 21(7): p. 1045-69. (Non Patent Document 53), as well as a compound represented by the following structural formula 1, a compound represented by the following structural formula 2, and a compound represented by the following structural formula 3. The compound represented by the following structural formula 1 is a MEK1/2-selective inhibitor, and is referred to as SMK-17 (Daiichi Sankyo Company, Limited). The compound represented by the following structural formula 2 is referred to as U0126 (Sigma). The compound represented by the following structural formula 3 exhibits inhibitory activity for MAPK in addition to MEK, and is referred to as PD184352.

structural formula 1

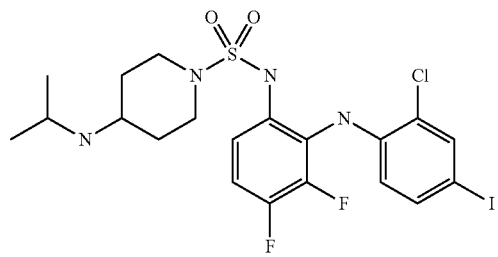

structural formula 2

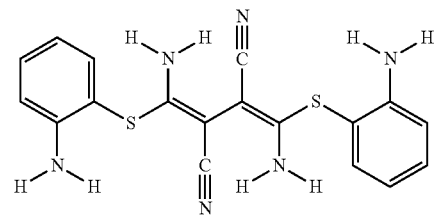

structural formula 3

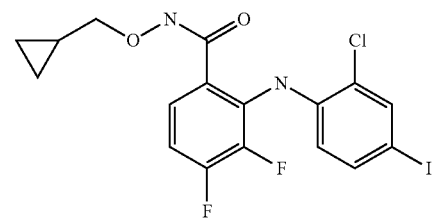

The compound that inhibits BRAF may be exemplified by a compound represented by the following structural formula 4. The compound is a BRAF-selective inhibitor referred to as SB590885.

structural formula 4

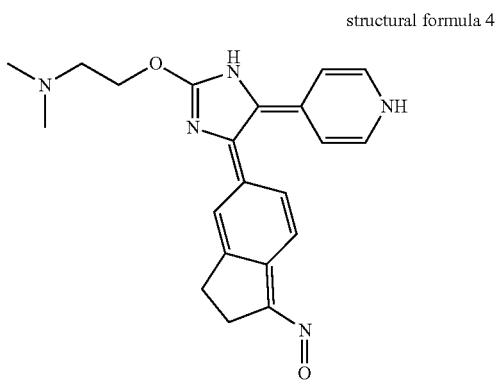 [SMILES: CN(C)CCOc1n/c(=c2/ccc3c(c2)CCC=3N=O)c(=C2C=CNC=C2)[nH]1]

A cancer disease to which the method according to the present invention is applicable can be a cancer disease in which tumor cells having an activated Wnt/β-catenin signaling pathway is detected, and is particularly preferably a cancer disease in which tumor cells having activated β-catenin are detected. Examples of such cancer disease may include a cancer disease in which tumor cells having an active β-catenin mutation are detected, and a cancer disease in which tumor cells having an N287S substitution mutation are detected. The active β-catenin mutation or the N287S substitution mutation is detected in a wide variety of cancer tissues and malignant tumor cell lines. Specific examples of the cancer disease to which the method according to the present invention is applicable may include colorectal cancer, liver cancer, skin cancer, lung cancer, kidney cancer, prostate cancer, duodenum cancer, ovary cancer, uterus corpus cancer, uterus cervix cancer, gallbladder cancer, pancreatic cancer, breast cancer, stomach cancer, oral cancer, tongue cancer, pharyngeal cancer, esophagus cancer, bronchus cancer, laryngeal cancer, bladder cancer, renal pelvis cancer, and ureter cancer. Of those, colorectal cancer, liver cancer, skin cancer, lung cancer, kidney cancer, prostate cancer, duodenum cancer, ovary cancer, and uterus corpus cancer are preferred.

In a cancer patient selected as having responsiveness to cancer treatment with the compound that inhibits a MAPK signaling pathway by the method according to the present invention, it can be considered that the administration of a therapeutically effective amount of the compound that inhibits a MAPK signaling pathway induces apoptosis in a tumor, resulting in tumor regression.

The compound that inhibits a MAPK signaling pathway is administered to a cancer patient by itself or as a composition containing the compound. The composition is produced as a pharmaceutical composition containing, in addition to the active ingredient, one kind or two or more kinds of pharmaceutical carriers such as a filler, an expander, a binder, a wetting agent, a disintegrant, a surfactant, a lubricant, a diluent, and an excipient to be generally used depending on the usage forms of a preparation. The amount of the active ingredient contained in the pharmaceutical composition is appropriately selected from a wide range, and it is appropriate that the amount be set to fall within a range of generally from about 0.00001 to 70% by weight, preferably from about 0.0001 to 5% by weight.

A dose range is not particularly limited and is appropriately selected depending on, for example, the effectiveness of an ingredient to be contained, a dosage form, an administration route, the kind of a disease, the properties of a subject (e.g., body weight, age, medical conditions, and the presence or absence of use of other pharmaceuticals), and the judgement of a doctor in attendance. In general, an appropriate dose falls within, for example, a range of from about 0.01 μg to about 100 mg, preferably from about 0.1 μg to about 1 mg per kg of body weight of a subject. However, these doses may be changed using a general routine experiment for optimization well known in the art. The dosage may be divided so that the administration may be performed once to several times a day. Alternatively, the administration may be performed intermittently at a frequency of once every several days or several weeks.

As the administration route, any of systemic administration and local administration may be selected. In this case, an appropriate administration route is selected depending on, for example, diseases and symptoms. For example, as a parenteral route, there are given subcutaneous administration, intradermal administration, and intramuscular administration in addition to general intravenous administration and intraarterial administration. Alternatively, oral administration may be adopted as the administration route. Further, transmucosal administration or transdermal administration may be performed. In addition, direct intratumoral administration may be adopted.

Various forms may be selected as the dosage form depending on purposes. Typical examples thereof include: a solid dosage form such as a tablet, a pill, a powder, a powdery preparation, a fine granule, a granule, or a capsule; and a liquid dosage form such as an aqueous solution preparation, an ethanol solution preparation, a suspension, a fat emulsion, a liposome preparation, a clathrate such as cyclodextrin, a syrup, or an elixir. Depending on administration routes, those dosage forms are further classified into an oral preparation, a parenteral preparation (an infusion or an injection), a transnasal preparation, an inhalant, a transvaginal preparation, a suppository, a sublingual preparation, eye drops, ear drops, a salve, a cream, a preparation for transdermal absorption, a preparation for transmucosal absorption, and the like, and may each be blended, formed, and prepared according to general methods.

The present invention also relates to a reagent and reagent kit to be used in the above-mentioned prediction method according to the present invention. The reagent according to the present invention is a reagent for detecting any one of mutations selected from the group consisting of (i) an active mutation of β-catenin and (ii) a substitution mutation of an asparagine residue to a serine residue at position 287 in an amino acid sequence of β-catenin. The reagent kit according to the present invention is a reagent kit including any one or two or more reagents out of such reagents in a separately packaged form.

The reagent according to the present invention is preferably a reagent for detecting one or more β-catenin mutations selected from the following:

(1) a substitution mutation of a serine residue at position 33, a serine residue at position 37, a threonine residue at position 41, or a serine residue at position 45 to an amino acid residue other than a serine residue or a threonine residue;

(2) a deletion mutation of a serine residue at position 33, a serine residue at position 37, a threonine residue at position 41, or a serine residue at position 45; and (3) a substitution of an asparagine residue to a serine residue at position 287.

The reagent according to the present invention is more preferably a reagent for detecting one or more β-catenin mutations selected from the following:

(4) a substitution mutation of a serine residue at position 33 or a serine residue at position 45 to an amino acid residue other than a serine residue or a threonine residue;

(5) a deletion mutation of a serine residue at position 45; and (6) a substitution of an asparagine residue to a serine residue at position 287.

A more specific example of the reagent according to the present invention is an oligonucleotide primer or oligonucleotide probe that is used in the method of detecting the mutation of β-catenin gene. Another example of the reagent according to the present invention may be an antibody that is used in the method of detecting the amino acid mutation of β-catenin.

The oligonucleotide primer may be any specific oligonucleotide primer designed so as to enable the specific amplification of the nucleotide sequence of the whole or a partial region containing a nucleotide at a mutation site of β-catenin gene or a mutant thereof. The specific oligonucleotide primer is a probe that can hybridize with a target of interest, that is, a nucleic acid of a partial region of the nucleotide sequence of the β-catenin gene or mutant thereof, or its complementary sequence, and does not substantially hybridize with a non-target nucleic acid, under appropriate hybridization or washing conditions. The appropriate hybridization or washing conditions may conform to, for example, methods described in the book (Non Patent Document 54) and the like. Such primer may be appropriately designed based on nucleotide sequence information of the β-catenin gene having a mutation, and may be acquired by chemical synthesis according to a conventional method. The design of the primer may be performed by using a method known per se or a well-known software for design.

An example of the oligonucleotide primer may be an oligonucleotide consisting of 10 to 60, preferably 15 to 30, more preferably 18 to 25 consecutive nucleotides, which hybridizes with part of a complementary sequence to the nucleotide sequence of a 5'-side region of a mutation site of the β-catenin gene having a mutation. As the size of the primer becomes smaller, the specificity for a target nucleotide sequence with which the primer hybridizes becomes higher but the binding affinity become slower. In contrast, as the size becomes larger, the binding affinity becomes higher but the specificity becomes lower. Therefore, an oligonucleotide primer having the above-mentioned size is appropriate. Such oligonucleotide primer is preferably used as an oligonucleotide primer set in combination with an oligonucleotide primer having the above-mentioned size and consisting of consecutive nucleotides, which hybridizes part of the nucleotide sequence of a 3'-side region of a mutation site of the β-catenin gene having a mutation. When the PCR is performed using such primer set, a nucleic acid of a region including a nucleotide at a mutation site of the β-catenin gene having a mutation is amplified. Whether or not the β-catenin gene in the test sample has a mutation may be detected by determining the nucleotide sequence of the amplified product by the DNA sequencing method described above.

The oligonucleotide primer may also be exemplified by an oligonucleotide consisting of 10 to 60, preferably 15 to 30, more preferably 18 to 25 consecutive nucleotides, which hybridizes with a nucleic acid consisting of a consecutive partial nucleotide sequence containing a mutation site of the β-catenin gene having a mutation, or a nucleic acid formed of a partial nucleotide sequence of wild-type β-catenin gene, the partial nucleotide sequence consisting a nucleotide at the position in which a mutation of interest is present, or its complementary oligonucleotide. Such oligonucleotide or its complementary oligonucleotide is not limited to one having the same nucleotide sequence as the nucleotide sequence of a partial region of the β-catenin gene having a mutation, and may be an oligonucleotide having high sequence homology or its complementary oligonucleotide as long as a mutation of interest present in β-catenin gene can be detected under appropriate hybridization or washing conditions. The oligonucleotide having high sequence homology refers to one having 80% or more, preferably 90% or more, more preferably 95% or more sequence homology, or one with difference of 1 to 10 nucleotide(s), preferably 1 to 5 nucleotide(s), more preferably 1 or 2 nucleotide(s), still more preferably 1 nucleotide. The detection of the mutation of β-catenin gene may be performed by amplifying a nucleic acid using such primer and detecting the presence or absence of the amplified product. When the amplified product is found by an oligonucleotide primer designed based on sequence information on the β-catenin gene having a mutation, the β-catenin gene in the test sample can be determined to have a mutation of interest. When the amplified product is not found or its amount is small as compared to a control, the β-catenin gene in the test sample can be determined to have no mutation that can be detected with the primer. When the amplified product is found by an oligonucleotide primer designed based on sequence information on wild-type β-catenin gene, the β-catenin gene in the test sample can be determined to have no mutation of interest. When the amplified product is not found or its amount is small as compared to a control, the β-catenin gene in the test sample can be determined to have a mutation.

The oligonucleotide probe is a specific oligonucleotide probe for any one of the above-mentioned mutations of β-catenin gene. The specific oligonucleotide probe is a probe that can hybridize with a target of interest, i.e., a partial region of the nucleotide sequence of a β-catenin gene mutant, the region including a nucleotide at a site in which any one of the above-mentioned mutations is present, and does not substantially hybridize with a non-target nucleic acid, under appropriate hybridization or washing conditions. A β-catenin gene mutant may be detected by detecting the hybridization of such oligonucleotide probe with a target gene. The appropriate hybridization or washing conditions may conform to, for example, methods described in the book (Non Patent Document 54) and the like.

The oligonucleotide probe may be any oligonucleotide probe designed so as to specifically hybridize with the nucleotide sequence of the whole, preferably a partial region containing a nucleotide at a mutation site of the β-catenin gene having a mutation. For example, there is given an oligonucleotide consisting of 15 or more, preferably 15 to 500, more preferably 18 to 200, still more preferably 18 to 50 consecutive nucleotides, or its complementary oligonucleotide, which hybridizes with the nucleotide sequence of a region containing a nucleotide at a position of the β-catenin gene having a mutation in which the mutation is present. As the size of the probe becomes smaller, the specificity for a target nucleotide sequence with which the probe hybridizes becomes higher but the binding affinity becomes lower. In contrast, as the size of the probe becomes larger, the binding affinity becomes higher but the specificity becomes lower. Therefore, an oligonucleotide probe having the above-mentioned size is appropriate. Such oligonucleotide or its complementary oligonucleotide may be appropriately designed based on nucleotide sequence information on the β-catenin gene having a mutation or wild-type-catenin gene, and may be acquired by chemical synthesis according to a conventional method. Such oligonucleotide or its complementary oligonucleotide is not limited to one having the same nucleotide sequence as the nucleotide sequence of a partial region of β-catenin gene, and may be an oligonucleotide having high sequence homology or its complementary oligonucleotide as long as a mutation of interest present in the β-catenin gene is detected under appropriate hybridization or washing conditions. The oligonucleotide having high sequence homology refers to one having 80% or more, preferably 90% or more, more preferably 95% or more sequence homology, or one with difference of 1 to 10 nucleotide(s), preferably 1 to 5 nucleotide(s), more preferably 1 or 2 nucleotide(s), still more preferably 1 nucleotide. When the hybridization of the oligonucleotide probe designed based on nucleotide sequence information on the β-catenin gene having a mutation is found, the β-catenin gene in the test sample can be determined to have a mutation of interest. When the hybridization is not found, the β-catenin gene in the test sample can be determined to have no mutation of interest. When the hybridization of the oligonucleotide probe designed based on nucleotide sequence information on the wild-type β-catenin gene is found, the β-catenin gene in the test sample can be determined to have no mutation of interest. When the hybridization is not found, the β-catenin gene in the test sample can be determined to have a mutation of interest.

The oligonucleotide probe and the oligonucleotide primer may each contain a nucleotide constituting an additional sequence, i.e., a nucleotide sequence not complementary to the β-catenin gene to be detected, in such a range that the specific detection of the mutation of the β-catenin gene is not disturbed.

In addition, the oligonucleotide probe and the oligonucleotide primer may each be labeled with an appropriate labeling agent such as a radioisotope, an enzyme, a fluorescent substance, a light-emitting substance, or biotin. Use of the labeled oligonucleotide probe and oligonucleotide primer may make it easy to detect their hybridization with a target gene. Preferred examples of the radioisotope may include $^{125}I$, $^{131}I$, $^{3}H$, $^{14}C$, $^{32}P$, $^{33}P$, and $^{35}S$. Preferred examples of the enzyme may include β-galactosidase, β-glucosidase, alkaline phosphatase, peroxidase, and malate dehydrogenase. Preferred examples of the fluorescent substance may include fluorescamine and fluorescein isothiocyanate. Preferred examples of the light-emitting substance may include luminol, a luminol derivative, luciferin, and lucigenin. Alternatively, in the vicinity of a reporter fluorescent dye such as FAM™ or VIC™, a quencher (quenching substance) for absorbing fluorescence energy emitted from the fluorescent dye may be further bound. In such embodiment, the fluorescent dye and the quencher separate from each other in a detection reaction and emitted fluorescence is detected.

The antibody may be any antibody as long as the antibody specifically binds to a β-catenin mutant. In addition, an isotype thereof may be any isotype, preferably an IgG antibody. Such antibody may be produced using as an antigen a desired β-catenin mutant, specifically a β-catenin mutant having any one of the above-mentioned amino acid mutations. The antigen may be a full-length protein of a β-catenin mutant, or may be a partial peptide thereof, the peptide consisting of a region containing a site in which an amino acid mutation is present. The antigen is consisting of at least 8, preferably at least 10, more preferably at least 12, still more preferably 15 or more amino acids. Such full-length protein and partial peptide may be produced as: cells in which a nucleic acid encoding the protein or peptide is expressed by a general genetic engineering technique (e.g., Non Patent Documents 54 to 56); a cell-free synthesis product; or a chemical synthesis product. Alternatively, the full-length protein and partial peptide may be prepared from the cells or living organism-derived samples, or may be purified products thereof.

The production of the antibody may be performed by utilizing an antibody production method known per se. For example, the antibody is obtained by administering to an animal the antigen in the presence or absence of an adjuvant, alone, or after the antigen has been bound to a carrier, to thereby perform immune induction such as a humoral immune response and/or a cellular immune response. The carrier is not particularly limited as long as the carrier itself does not exhibit any adverse action on a host and can enhance antigenicity. Examples thereof may include cellulose, a polymerized amino acid, albumin, and keyhole limpet hemocyanin. Examples of the adjuvant may include Freund's complete adjuvant (FCA), Freund's incomplete adjuvant (FIA), Ribi (MPL), Ribi (TDM), Ribi (MPL+TDM), *Bordetella pertussis* vaccine, muramyl dipeptide (MDP), and an aluminum adjuvant (ALUM), and combinations thereof. For example, a mouse, a rat, a rabbit, a goat, and a horse are suitably used as the animal for immunization.

The antibody may be any of a monoclonal antibody and a polyclonal antibody. The polyclonal antibody may be acquired from serum of an animal subjected to immunization means by an antibody collection method known per se. As preferred antibody collection means, there is given an immunoaffinity chromatography method. The monoclonal antibody may be produced by using a known method such as a hybridoma method (Non Patent Document 57). The selection of a hybridoma for producing an antibody of interest may be performed, for example, by screening by a known method (Non Patent Documents 58 and 59). That is, a desired antibody may be obtained by: performing a test on binding between a monoclonal antibody produced by a hybridoma and a β-catenin mutant of interest; and selecting an antibody specifically binding to the β-catenin mutant of interest.

The antibody may be any of an intact antibody and an antibody fragment. The "intact antibody" means an antibody composed of a tetramer structural unit similar to that of a natural antibody. The "antibody fragment" means a fragment containing part of the intact antibody, for example, an antigen-binding region or variable region of the intact antibody. Examples of the antibody fragment include a Fab fragment, a $Fab_1$ fragment, a $F(ab')_2$ fragment, a Fv fragment, a diabody, a linear antibody, a single-chain antibody molecule, and a multi-specific antibody to be formed from antibody fragments. The "Fab fragment" is an antigen-binding fragment having a single antigen-binding site, and two identical Fab fragments each having a single antigen-binding site may be produced from one antibody by subjecting the antibody to papain digestion. The "$F(ab')_2$ fragment" is an antibody fragment that may be produced by subjecting an antibody to pepsin treatment, and is still capable of cross-linking antigens. The "Fv fragment" is an antibody fragment containing a complete antigen recognition site and antigen-binding site, and is composed of a dimer of one heavy chain variable domain and one light chain variable domain closely bound through a non-covalent bond. Half of the Fv containing a single variable domain or only antigen-specific three CDRs can recognize an antigen and can bind thereto. A "single-chain Fv" or "sFv" antibody fragment that is a single-chain antibody molecule has a feature of containing a VH domain and VL domain of an antibody, in which these domains are present in a single polypeptide chain. A Fv polypeptide may further contain a polypeptide linker, which allows sFv to form a desired structure for antigen binding, between the VH domain and the VL domain. The term "diabody" refers to a small antibody fragment having two antigen-binding sites, and this fragment contains a heavy chain variable domain (VH) linked to a light chain variable domain (VL) on the same polypeptide chain (VH-VL). A short linker is used for enabling association between the two domains on the same chain, which allows association of the domains with complementary domains on the other chain to produce two antigen-binding sites.

The oligonucleotide primer, oligonucleotide probe, and antibody to be used as the reagent according to the present invention may be ones provided as a nucleic acid array or antibody array by being bound onto an appropriate support. The support is not particularly limited and may be of any shape or material as long as a nucleic acid or a protein can be fixed onto the support. Specific examples thereof may include a support made of an inorganic material such as glass, a silicon wafer, beads, a resin, or a metal, and a support made of a natural polymer material such as nitrocellulose or a synthetic polymer material such as nylon.

Hereinafter, the present invention is described more specifically by way of Examples, but is in no way limited to the following Examples.

First, materials and methods used in Examples are described.

The following cell lines were used in the Examples: A375 cells, A2058 cells, HT29 cells, colo-205 cells, SK-MEL-1 cells, colo-201 cells, LS-174T cells, HCT_116 cells, SW620 cells, DLD-1 cells, A549 cells, OVCAR-5 cells, AN3-CA cells, DU145 cells, NCI-N87 cells, JIMT-1 cells, SW48, SW480, A431 cells, HeLa cells, EC109 cells, Ms-1 cells, LNCaP cells, and PC-3 cells.

Drugs used are MEK inhibitors SMK-17 (manufactured by Daiichi Sankyo Company, Limited) and U0126 (manufactured by Sigma), a PI3K inhibitor LY294002 (manufactured by Sigma), a MEK and MAPK inhibitor PD184352 (synthesized by Daiichi Sankyo Company, Limited), a multikinase inhibitor sorafenib (synthesized by Daiichi Sankyo Company, Limited), and a BRAF selective inhibitor SB590885 (synthesized by Daiichi Sankyo Company, Limited).

The cell lines were cultured under condition of 37° C. and 5% $CO_2$ in a culture medium that is RPMI 1640 medium (manufactured by Nissui Pharmaceutical Co., Ltd.) subjected to high-pressure steam sterilization and supplemented with 0.1 g/L of kanamycin (manufactured by Sigma), 100 units/mL of penicillin F, and 0.3 g/L of L(+)-glutamine (manufactured by Wako) each subjected to filter sterilization, 2.5 g/L of $NaHCO_3$ subjected to high-pressure steam sterilization, and 10% of fetal bovine serum (FBS). The cells were subcultured every 3 days in order to prevent the cells from becoming overconfluent that causes transformation of the cells during the culture. After the removal of the culture medium, the cells were washed with a $Ca^{2+}$- and $Mg^{2+}$-free phosphate buffer solution (PBS$^-$: 8.0 g/L of NaCl, 0.2 g/L of KCl, 0.916 g/L of $Na_2HPO_4$, 0.2 g/L of $KH_2PO_4$), and the cells were detached by treatment with a trypsin-ethylenediaminetetraacetic acid (EDTA) solution (0.75 g/L of trypsin, 8.0 g/L of NaCl, 0.4 g/L of KCl, 0.0475 g/L of $Na_2HPO_4$, 0.06 g/L of $KH_2PO_4$, 1.0 g/L of glucose, 0.02 g/L of phenol red, 0.35 g/L of $NaHCO_3$, 0.2 g/L of EDTA) and subcultured.

A cell growth-suppressive activity test was performed in both of two-dimensional culture and three-dimensional culture. First, a plate for three-dimensional culture was produced. Specifically, poly(2-hydroxyethyl methacrylate) (hereinafter abbreviated as poly-HEMA, manufactured by Sigma) was added to 95% ethanol so that the concentration was 5 mg/mL, and dissolved therein at 37° C. overnight. The solution was used as a poly-HEMA solution. The solution was loaded into a 96-well plate (manufactured by Nunc) at 50 μL/well. The plate was dried at 37° C. to produce a plate for three-dimensional culture coated with poly-HEMA.

The two-dimensional culture (hereinafter sometimes referred to as 2D culture) and the three-dimensional culture (hereinafter sometimes referred to as 3D culture) were performed by seeding the cells in a 96-well plate at $1 \times 10^3$ cells/150 μL/well and $2 \times 10^3$ cells/75 μL/well, respectively, and performing drug treatment on the following day. The total volume was set to 200 μL in the two-dimensional culture, and the total volume was set to 100 μL in the three-dimensional culture. Cell growth was measured by measuring intracellular ATP amounts at the time of the drug treatment and 72 hours after the drug treatment. Specifically, after the removal of the culture medium at 100 μL/well, CellTiter-Glo (manufactured by Promega) was added at 50 μL/well in the two-dimensional culture, and CellTiter-Glo was added at 50 μL/well in the three-dimensional culture. After the addition, the plate was shaken with a shaker for 2 minutes and left to stand still at room temperature for 10 minutes. The total volume of each well was transferred to a white 96-well plate (manufactured by Nunc) and measured for its light emission intensity with a Wallac 1420 multilabel counter (manufactured by Perkin Elmer). From the resultant light emission amount, a growth ratio (Growth (%)) relative to a non-drug-treated sample after 72 hours was determined using the following mathematical formula 1 and mathematical formula 2. In addition, a drug concentration causing 50% growth inhibition was defined as $GI_{50}$. It should be noted that in the formula 1 and the formula 2, "comp day4" represents a light emission amount of a sample 72 hours after drug treatment, "blank" represents a light emission amount of a culture medium alone, "control day4" represents a light emission amount of a non-drug-treated sample after 72 hours, and "control day1" represents a light emission amount of a sample at the time of drug treatment.

mathematical formula 1

$0 \sim 100\%$ $$\text{Growth (\%)} = \frac{(\text{comp day4} - \text{blank})}{(\text{control day4} - \text{blank})} \times 100$$

$0 \sim -100\%$ $$\text{Growth (\%)} = \frac{(\text{comp day4} - \text{blank})}{(\text{control day1} - \text{blank})} \times 100 - 100$$

A correlation between the results in the 2D culture and the results in the 3D culture was evaluated with a Pearson's product-moment correlation coefficient.

The resultant product-moment correlation coefficient was used to perform a significance test. When assuming that a null hypothesis $H_0$ is "population correlation coefficient=0," that is, "there is no correlation," and the hypothesis is not rejected, it can be said that there is no correlation. In contrast, when the hypothesis is rejected, it can be said that there is a correlation. When the number of samples is represented by n and a sample correlation coefficient is represented by r, a test statistic $t_0$ is represented by the following mathematical formula 3. This follows a t-distribution with a degree of freedom of n−2, and the null hypothesis is rejected if $t_0 > t(n-2, \alpha)$, where α represents a critical rate.

mathematical formula 3

$$t_0 = \frac{|r|\sqrt{n-2}}{\sqrt{1-r^2}}$$

Western blotting was performed to detect a protein as described below. First, a sample was obtained by seeding cells in a 6-well plate (manufactured by Greiner), followed by treating with a drug, and washed with PBS− containing $Na_3VO_4$ (1 mM) on ice, and then added with an appropriate amount of RIPA buffer (25 mM HEPES, 1.5% Triton X-100, 1.0% sodium deoxycholate, 0.1% sodium dodecyl sulfate (hereinafter abbreviated as SDS), 0.5 M NaCl, 5 mM EDTA, 50 mM NaF, 0.1 mM $Na_3VO_4$, 0.1 mg/mL of leupeptin, 1 mM phenylmethylsulfonyl fluoride (hereinafter abbreviated as PMSF): pH 7.8). The cells were solubilized and collected and then were left to stand still on ice for 30 minutes. Centrifugation treatment was performed at 13,000 g for 15 minutes, and the resultant supernatant was used as a cell extract.

In the detection of non-adherent cells and apoptosis-related proteins, a culture medium was collected in a 15-mL tube, and the cells were washed with PBS− containing $Na_3VO_4$ (1 mM). After that, centrifugation was performed at 1,000 g for 5 minutes, and the supernatant was removed. The residue, was added with 1 mL of PBS− to suspend the cells. The suspension was transferred to a 1.5-mL tube and then subjected to centrifugation at 13,000 g for 1 minute, and the supernatant was removed. An appropriate amount of RIPA buffer was added to adherent cells so as to solubilize the cells. The cells were collected and then left to stand still on ice for 30 minutes. Centrifugation was performed at 13,000 g for 15 minutes, and the resultant supernatant was used as a cell extract.

The cell extracts, which protein concentration was set to a uniform one, were added with a half amount of 3×SDS sample buffer (150 mM Tris, 30% glycerol, 3% SDS, 1.5 mg/100 mL of bromophenol blue, 100 mM 2-mercaptoethanol: pH 6.8), and boiled at 100° C. for 5 minutes. The resultant was used as a sample for SDS-polyacrylamide gel electrophoresis (SDS-PAGE).

The sample was subjected to electrophoresis with a polyacrylamide gel and transferred onto a polyvinylidene fluoride (PVDF) membrane (Hybond P: manufactured by Millipore), and then blocked with a TBS-Tween solution (20 mM Tris-HCl, 137 mM NaCl, 0.1% Tween 20:pH 7.6) containing bovine serum albumin (abbreviated as BSA) or skim milk for 30 minutes. A primary antibody was added to each solution at a ratio of 1:1,000, followed by shaking at 4° C. overnight. After washing with a TBS-Tween solution, the resultant was immersed in a secondary antibody solution (1:5000, 3% skim milk) containing an anti-rabbit horseradish peroxidase antibody (manufactured by Amersham) or an anti-mouse horseradish peroxidase antibody (manufactured by Amersham) and shaken at room temperature for 1 hour. After washing with a TBS-Tween solution, color development with an electrochemiluminescence (ECL) color development liquid (manufactured by Millipore) was performed for detection with LAS1000 (manufactured by Fuji film). For the electrophoresis, running buffer (25 mM Tris, 192 mM glycine, 0.1% SDS) was used. For the transfer, transfer buffer (25 mM Tris, 192 mM glycine, 20% methanol) was used.

A cell cycle measurement was performed by propidium iodide (PI) staining as described below. First, cells were subjected to drug treatment after 24 hours from seeding thereof in a 6-well plate. After collecting the culture medium and trypsinized cells, they were subjected to centrifugation at 1,000 g for 5 minutes, and the supernatant was removed. 1 mL of PBS− was added to suspend the cells. The suspension was transferred to a 1.5-mL tube and then subjected to centrifugation treatment at 13,000 g for 1 minute, and the supernatant was removed. 200 μL of PBS− was added to the residue to suspend the cells, and 1 mL of ice-cold 70% ethanol was added. Then, the cells were vortexed and immobilized at 4° C.

The immobilized cells were subjected to centrifugation at 1,000 g for 5 minutes, and the supernatant was removed. 1 mL of a PBS− solution containing 10 μg/mL of RNase was added to the residue to suspend the cells, which was left to stand still at 37° C. for 20 minutes. After that, centrifugation was performed for 5 minutes, and then the supernatant was removed. 500 L of a PBS− solution containing PI (50 μg/mL, manufactured by Wako) was added to the residue to suspend the cells. The total volume thereof was passed through a nylon mesh (φ=42 μm) and used as a sample. An intracellular DNA content was detected with PMT4 of a flow cytometer (manufactured by Beckman Coulter) to measure a cell cycle.

A TOPFLASH reporter assay was performed as described below. Cells were seeded in a 6-well plate (2 mL/well) so that the cells became subconfluent on the following day. Gene transfection was performed on the following day. A TCF reporter plasmid (TOPFLASH, manufactured by Millipore), a TK promoter-renilla luciferase reporter plasmid (manufactured by Promega), and Plus Reagent (manufactured by Sigma) were added to 500 μL of OPTI-MEM I (2.44 g/L of $NaHCO_3$, 13.6 g/L of OPTI-MEM I (manufactured by Gibco)), and were mixed by inversion. The mixture was left to stand still at room temperature for 5 minutes. After that, Lipofectamine LTX (manufactured by Sigma) was added, and the mixture was left to stand still at room temperature for 30 minutes. The total volume thereof was added to the culture medium to culture the cells. After 24 hours, the cells were seeded again in a white 96-well plate at $2 \times 10^4$ cells/75 μL/well. Drug treatment was performed on the following day. The total volume was set to 100 μL, and the cells were cultured for 24 hours. After that, the culture medium in each well was removed and replaced with PBS− at 100 μL/well, and the cells were frozen at −80° C., except for the colo-201 cells which were frozen at −80° C. directly without the replacement with PBS−.

At the time of an assay, the cells were thawed and added with Dual-Gloluciferase Reagent (manufactured by Promega) at 50 L/well, which was left to stand still for 5 minutes. After that, the light emission intensity of firefly luciferase was measured with a Wallac 1420 multilabel counter. Next, Dual-Glo Stop & Glo Reagent (manufactured by Promega) was added at 50 μL/well, and the whole was left to stand still for 5 minutes. After that, the light emission intensity of renilla luciferase was measured with a Wallac 1420 multilabel counter. From the data obtained, TCF4 transcriptional activity (TCF transcriptional activity) was determined using the following mathematical formula 4.

$$TCF4 \text{ transcriptional activity} = \frac{\text{firefly luc (CPM)}}{\text{Renilla luc (CPM)}}$$

mathematical formula 4

The knockdown of β-catenin was performed using siRNA. Specifically, the knockdown of β-catenin was performed by a reverse transfection method using Stealth RNAi (manufactured by invitrogen). The sequence of the used siRNA is shown below: 5'-AUUACUAGAGCAGACA-GAUAGCACC-3' (SEQ ID NO: 3).

To 100 μL of OPTI-MEM I, HiPerFect (manufactured by Qiagen) diluted 300-fold and the siRNA at a final concentration of 5 nM were added, and the contents were gently mixed and left to stand still at room temperature for 10 minutes. In addition, Stealth RNAi Negative control (manufactured by Invitrogen) was used as a control. The mixed solution was added to each well of a 12-well plate (manufactured by Nunc) or a 60-mm dish (manufactured by Greiner), and a cell suspension ($1.2 \times 10^5$ cells/600 μL/well for the 12-well plate and $1.3 \times 10^5$ cells/2.4 mL/dish for the 60-mm dish) was seeded therein. On the following day, the culture medium was exchanged for a fresh one, and apoptosis-inducing activity was evaluated by measuring transfection efficiency by western blotting and measuring a cell cycle with a flow cytometer.

Gene transfection with dominant-negative-TCF4 and gene transfection with active β-catenin were performed as described below. First, cells (2 mL/well) were seeded in a 6-well plate so that the cells became subconfluent on the following day. The gene transfection was performed on the following day. 2.5 μg of a control vector (manufactured by Invitrogen) or a dominant-negative-TCF4 plasmid (hereinafter abbreviated as DN-TCF4, manufactured by Millipore) or an active β-catenin plasmid was added to 500 μL of OPTI-MEM I together with 2.5 μL of Plus Reagent, and mixed by inversion. The mixture was left to stand still at room temperature for 5 minutes. After that, 10 μL of Lipofectamine LTX was added, and the mixture was left to stand still at room temperature for 30 minutes. The total volume thereof was added to the culture medium to culture the cells. After 24 hours, the cells were seeded again, and various assays were performed.

EXAMPLE 1

Drug sensitivities to a MEK inhibitor SMK-17 were compared among cell lines. Specifically, 24 kinds of cell lines having protein mutations involved in various signaling pathways associated with cell growth were used to evaluate the growth-suppressive activity of a MEK inhibitor SMK-17 (Daiichi Sankyo Company, Limited) in two-dimensional culture and three-dimensional culture. In addition, a MEK inhibitor U0126 was used as a comparative material to evaluate the growth-suppressive activity in the same manner as above.

Growth-suppressive activity was evaluated by measuring an intracellular ATP amount in terms of luciferase light emission amount through use of CellTiter-Glo. Specifically, cells were subjected 24 hours after seeding thereof to drug treatment by adding SMK-17 and U0126 to culture media so that the final concentrations were 0.1, 0.3, 1.0, 3.0, 10, and 30 μM. 72 hours after the drug treatment, an intracellular ATP amount was measured using CellTiter-Glo. From the resultant light emission amount, a growth ratio was calculated, and a drug concentration causing 50% growth inhibition ($GI_{50}$) was further calculated. Based on the $GI_{50}$, a correlation between the result of the two-dimensional culture and the result of the three-dimensional culture was evaluated using a Pearson's product-moment correlation coefficient. Product-moment correlation coefficients r between the two-dimensional culture and the three-dimensional culture for the drugs were determined to be as follows: r=0.88 for SMK-17 and r=0.72 for U0126. A significance test was performed based on the product-moment correlation coefficients. As a result, the test statistics were as follows: r=8.0 for SMK-17 and r=4.5 for U0126. The number of samples n was 21. The null hypothesis was rejected in both the compounds based on t (19, 0.01)=2.9, which showed a correlation between the two-dimensional culture and the three-dimensional culture.

Next, in order to compare the gene mutations and drug sensitivities of cell lines, $-\log(GI_{50})$ was calculated from the $GI_{50}$ obtained for both drugs in the two-dimensional culture and the three-dimensional culture, and the value was expressed in a fingerprint pattern with an average value (MG-MID) being at the origin (Non Patent Document 50). In this connection, the cell lines having positive $-\log(GI_{50})$ values were regarded as high-sensitivity cell lines, and the cell lines having negative $-\log(GI_{50})$ values were regarded as low-sensitivity cell lines. In addition, regarding mutations of BRAF, K-ras, PTEN, β-catenin, and APC, the cell lines were divided into a mutant cell line group and a wild-type cell line group, and a significant difference in average value of $GI_{50}$ between the two groups was evaluated by a t-test.

As shown in FIG. 1, it was found in the growth-suppressive activity test of SMK-17 that the cell lines having active mutations of BRAF present upstream of MEK, i.e., A375, HT29, colo-205, and colo-201 each exhibited high sensitivity.

In addition, there was a significant difference at p<0.001 in average value of $GI_{50}$ between the active BRAF mutant cell line group and the wild-type cell line group. This fact suggested that the active BRAF mutation was a positive sensitivity-determining factor for SMK-17 as with the existing MEK inhibitors such as PD184352. Next, among the cell lines having active mutations of K-ras located upstream of BRAF, the LS-174T cells, the HCT_116 cells, the SW480 cells, and the SW620 cells were high-sensitivity cell lines, whereas the A549 cells, the OVCAR-5 cells, and the DLD-1 cells were low-sensitivity cell lines. In addition, there was no significant difference in average value of $GI_{50}$ between the active K-ras mutant cell line group and the wild-type cell line group. This fact suggested that the active K-ras mutation was not a sensitivity-determining factor for SMK-17. On the other hand, all of the PTEN-deficient cell lines AN3-CA, LNCaP, and PC-3 were low-sensitivity cell lines. There was no significant difference in average value of $GI_{50}$ between the PTEN-deficient cell line group and the wild-type cell line group, but the PTEN-deficient cell line A2058 having an active BRAF mutation had lower sensitivity than the other active BRAF mutant cell lines, suggesting that the PTEN deficiency was a negative sensitivity-determining factor for SMK-17. In addition, regarding BRAF, K-ras, and PTEN, the wild-type cell lines (A431, DU145, EC109, HeLa, Ms-1, NCI-N87, and JIMT-1) were low-sensitivity cell lines, suggesting that the cell growth of these cell lines did not depend on the MAPK signaling pathway. On the other hand, regarding BRAF, K-ras, and PTEN, despite the fact that most of the wild-type cells lines were low-sensitivity cell lines, the SW48 cells having wild-type BRAF, K-ras, and PTEN exhibited high sensitivity to SMK-17.

The SW48 cells, which have exhibited high sensitivity to SMK-17, are a cell line having wild-type BRAF, K-ras, and PTEN and having an active mutation of β-catenin. In view of this fact, when attention is focused on a mutation on the Wnt/β-catenin signaling pathway that includes β-catenin as a constituent factor, all of the active β-catenin mutant cell lines colo-205, colo-201, SK-MEL-1, LS-174T, HCT_116, and SW48 were high-sensitivity cell lines. In proteins involved in the Wnt/β-catenin signaling pathway, an APC mutation has also been reported. Among the APC mutant cell lines, colo-205, colo-201, SW480, and SW620 exhibited high sensitivity. In addition, the active β-catenin mutant cell line group, the APC mutant cell line group, and the active β-catenin and APC mutant cell line group were tested for significant differences in average value of $GI_{50}$ with respect to the wild-type cell line group which resulted in showing significant differences at $p<0.001$, $p<0.05$, and $p<0.01$, respectively. This fact suggested that the mutation on the Wnt/β-catenin signaling pathway was a positive sensitivity-determining factor for SMK-17.

Next, regarding U0126, which was a MEK inhibitor similar to SMK-17, 23 out of the 24 kinds of cell lines exhibited a tendency of drug sensitivity similar to that in the case of SMK-17. In addition, evaluation of a correlation between SMK-17 and U0126 was performed using each $GI_{50}$, which gives $r=0.82$ and $t_0=6.9$ as a result. In this case, the null hypothesis was rejected based on t $(22, 0.01)=2.8$, which showed a correlation between SMK-17 and U0126. In addition, there were significant differences in average value of the $GI_{50}$ regarding the active BRAF mutation, the active β-catenin mutation, the APC mutation, and the active β-catenin and APC mutation with respect to the wild-type cell line group at $p<0.001$, $p<0.01$, $p<0.01$, and $p<0.001$, respectively. This fact suggested that the active BRAF mutation and the mutation on the Wnt signaling pathway were positive sensitivity-determining factors for U0126 as well as SMK-17, while the PTEN deficiency was a negative sensitivity-determining factor.

The above-mentioned results revealed that the active β-catenin mutation was a positive sensitivity-determining factor for the MEK inhibitor SMK-17.

EXAMPLE 2

Cell cycle arrest mediated by a MEK inhibitor SMK-17 and its apoptosis-inducing activity were evaluated. Example 1 revealed that there exist cell lines to which SMK-17 exhibited high growth-suppressive activity. The growth-suppressive activity is probably due to cell cycle arrest or cell death such as apoptosis. In view of the foregoing, the influences of SMK-17 on the cell cycle and apoptosis of a high-sensitivity cell line were evaluated.

The evaluation of the cell cycle arrest mediated by SMK-17 and apoptosis-inducing activity thereof were performed by using a total of 9 cell lines including DLD-1, a low-sensitivity cell line having an active K-ras mutation and an APC mutation, in addition to the cell lines in which SMK-17 exhibited high growth-suppressive activity, i.e., A375 (active BRAF mutation), HT29 (active BRAF mutation, APC mutation), HCT_116 (active K-ras mutation, active β-catenin mutation), SW48 (active β-catenin mutation), colo-201 (active β-catenin mutation, APC mutation), LS-174T (active K-ras mutation, active β-catenin mutation), SW620 (active K-ras mutation, APC mutation), and SW480 (active K-ras mutation, APC mutation). The cells were subjected after 24 hours from seeding thereof to drug treatment involving adding SMK-17 to a culture medium so that the final concentrations were 0.1, 0.3, 1.0, 3.0, and 10 μM. 48 hours after the drug treatment, the cells were collected and subjected to ethanol fixation and PI staining to measure a DNA content with a flow cytometer. In addition, in order to measure the MEK inhibitory activity of SMK-17 in the drug-treated cells, the expression of ERK, phosphorylated ERK, and actin in the cells with SMK-17 was evaluated by western blotting 24 hours after the treatment. In addition, the expression amount of a target molecule being phosphorylated was calculated compared to the expression amount of a target molecule to evaluate the influence on a cell cycle at such a concentration of inhibiting the expression of the phosphorylation of the target molecule by 95% or more. Then, when an increase in sub-G1 population by 20% or more was found, it was determined that apoptosis was induced.

In the HCT_116 cells, SW48 cells, colo-201 cells, and LS-174T cells, all of which have active β-catenin mutations, the treatment with SMK-17 at such a concentration that the phosphorylation of ERK was completely inhibited, resulted in observation of remarkable increase in the sub-G1 population and DNA fragmentation. Specifically, in the HCT_116 cells, the SW48 cells, the colo-201 cells, and the LS-174T cells, the treatment with SMK-17 at concentrations of 10 μM, 10 μM, 1.0 μM, and 10 μM, respectively, resulted in observations of complete inhibition of ERK phosphorylation, and the induction of apoptosis indicated by an increase in sub-G1 population and DNA fragmentation.

On the other hand, in the A375 cells, the HT29 cells, and the SW480 cells, the treatment with SMK-17 at such a concentration that the phosphorylation of ERK was completely inhibited, resulted in observations of reduction in the ratios of an S population and a G2/M population to a large extent and remarkable G1 arrest, but not DNA fragmentation. Specifically, in the A375 cells, the HT29 cells, and the SW480 cells, the treatment with SMK-17 at concentrations of 1.0 μM, 3.0 μM, and 3.0 μM, respectively, resulted in observations of complete inhibition of ERK phosphorylation and cell cycle arrest. In the SW620 cells and DLD-1 cells treated with SMK-17 at such a concentration that the phosphorylation of ERK was completely inhibited, i.e., 1.0 μM, no influence on a cell cycle was observed.

Figure 2:
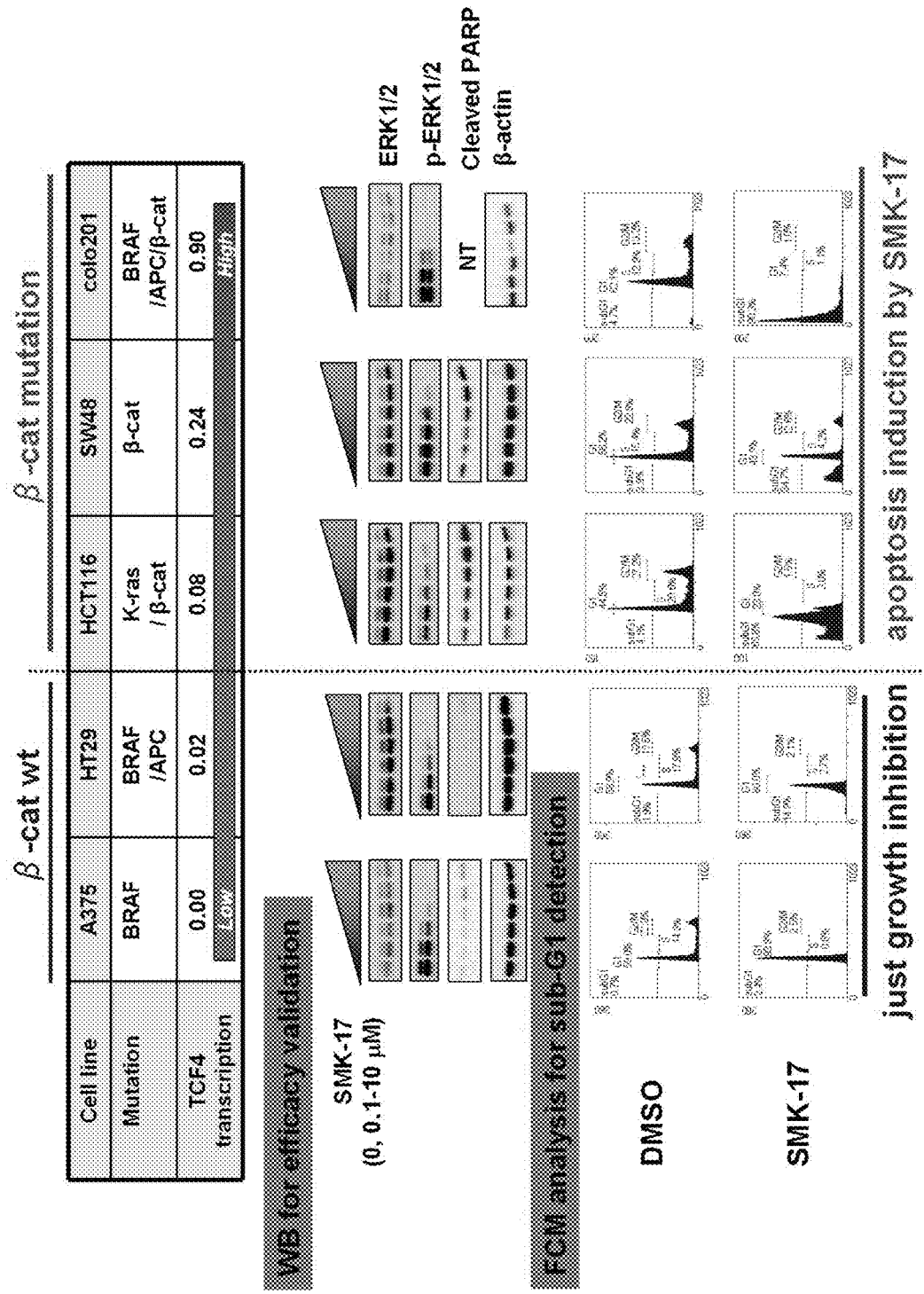
FIG. 2 shows that apoptosis induction by treatment with SMK-17 was observed in cell lines having active β-catenin mutations (represented by "β-cat mutation" in FIG. 2). Specifically, an increase in number of sub-G1 cells and DNA fragmentation, which indicated apoptosis induction, were observed in cell lines having active β-catenin mutations, HCT_116, SW48, colo-201, and LS-174T, when the cells were treated with SMK-17 at such a concentration that the phosphorylation of ERK was completely inhibited. On the other hand, a remarkable increase in number of G1-arrested cells was observed in cell lines having wild-type β-catenin (β-cat wt), A375 and HT29, but not observed a remarkable increase in number of sub-G1 cells, which indicated that only growth inhibition was induced. The upper panel shows proteins in which mutations were found in the cell lines used, and the TCF4 transcriptional activity in the cell lines. The middle panel shows the ERK phosphorylation inhibitory activity of SMK-17. The lower panel shows the results of detection of sub-G1 cells with a flow cytometer (FCM) (Example 2).

FIG. 2 shows typical results. The results revealed that the MEK inhibitor SMK-17 induced apoptosis selectively in the cell line having an active β-catenin mutation.

EXAMPLE 3

The apoptosis-inducing activity of a MAPK signaling pathway inhibitor was evaluated. In Example 2, it was revealed that the MEK inhibitor SMK-17 induced apoptosis selectively in the cell line having an active β-catenin mutation. MEK is a downstream factor in the MAPK signaling pathway. In view of the foregoing, the MAPK signaling pathway was inhibited by MAPK signaling pathway inhibitors other than SMK-17 to investigate their apoptosis-inducing activities.

The apoptosis-inducing activities of a MEK inhibitor PD184352, a multikinase inhibitor sorafenib, which inhibited, in particular, Raf (Non Patent Document 61), and a BRAF-selective inhibitor SB590885 were investigated using wild-type β-catenin cell lines A375 and HT29, an APC mutant cell line DLD-1, and active β-catenin mutant cell lines HCT_116 and SW48. The cells were treated with PD184352 at 0.1, 0.3, 1.0, 3.0, and 10 μM and sorafenib and SB590885 at 0.3, 1.0, 3.0, and 10 µM. 48 hours after the drug treatment, the cells were collected and subjected to ethanol fixation and PI staining to measure a DNA content with a flow cytometer. In addition, in order to measure target molecule inhibitory activity in the drug-treated cells, the expression of ERK, phosphorylated ERK, MEK, phosphorylated MEK, and actin in the cells was evaluated by western blotting 24 hours after the drug treatment. In addition, the expression amount of a target molecule being phosphorylated was calculated compared to the expression amount of a target molecule to evaluate the influence of each inhibitor on a cell cycle at such a concentration that the expression of the phosphorylation of the target molecule was inhibited by 95% or more. Then, when an increase in sub-G1 population by 20% or more was found, it was determined that apoptosis was induced.

Figure 3:
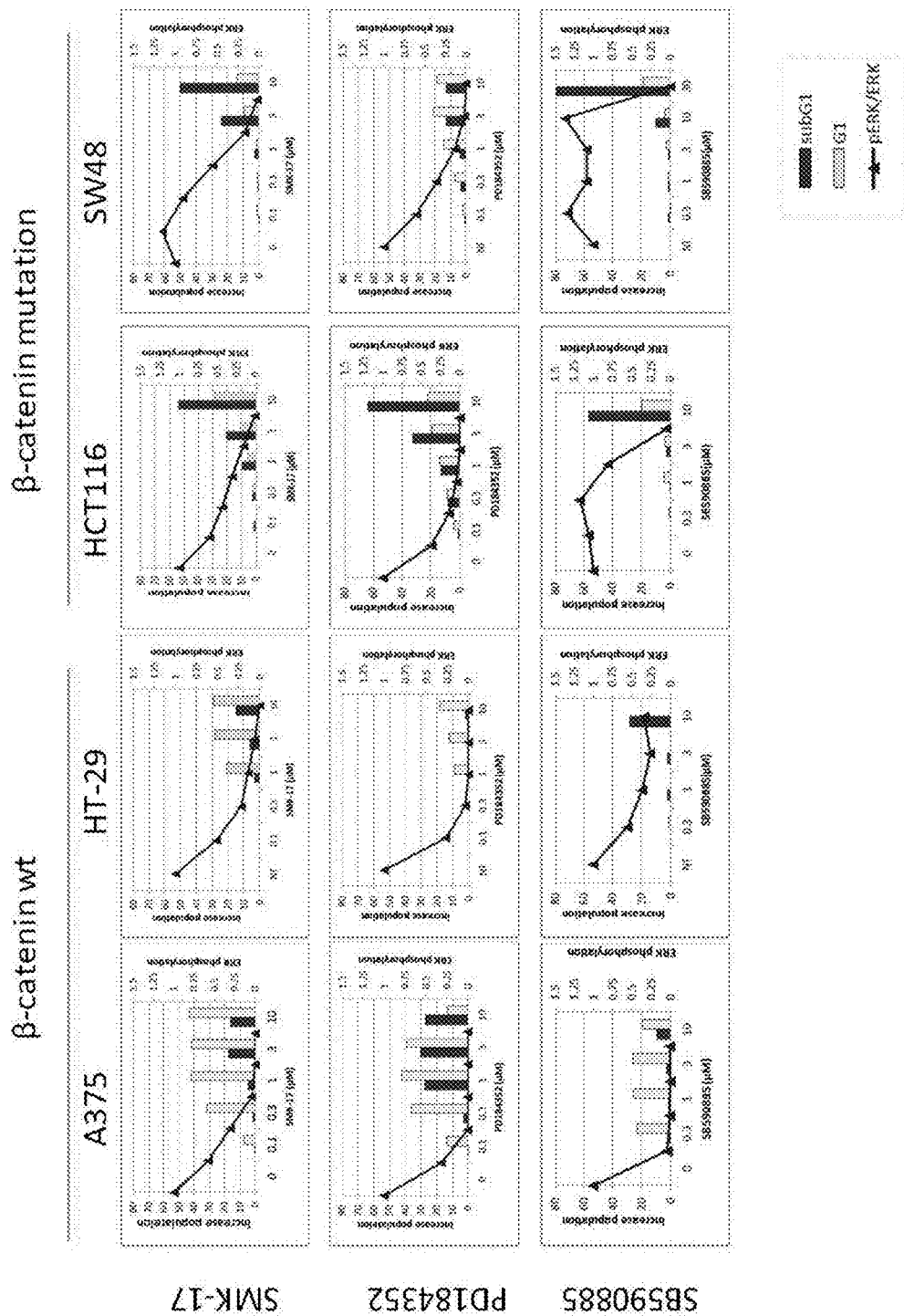
FIG. 3 shows that MEK inhibitors SMK-17 and PD184352 and a BRAF-selective inhibitor SB590885 each exhibited apoptosis-inducing activity in a cell line having an active β-catenin mutation, HCT_116 and/or SW48, at such a concentration that ERK phosphorylation was completely inhibited. On the other hand, these inhibitors did not induce apoptosis-inducing activity in a cell line having wild-type β-catenin, A375, at such a concentration that ERK phosphorylation was completely inhibited (Example 3).

As shown in FIG. 3, apoptosis was induced in the active β-catenin mutant cell lines HCT_116 and SW48 by the treatment with the MEK inhibitor PD184352 at such concentrations that the phosphorylation of ERK was completely inhibited, i.e., 3.0 µM and 3.0 µM, respectively. This fact revealed that PD184352 also inhibited MEK and induced apoptosis selectively in the active β-catenin mutant cells, as with SMK-17.

In addition, apoptosis was induced in the active β-catenin mutant cell line HCT_116 by the treatment with the BRAF-selective inhibitor SB590885 at such a concentration that the phosphorylation of MEK and ERK was completely inhibited, i.e., 10.0 µM. On the other hand, G1 arrest was induced but no apoptosis was induced in the β-catenin wild-type cell line A375 by the treatment with the BRAF-selective inhibitor SB590885 at such a concentration that the phosphorylation of MEK and ERK was completely inhibited, i.e., 1.0 µM. This fact revealed that SB590885 induced apoptosis selectively in the active β-catenin mutant cells.

Meanwhile, remarkable G1 arrest was induced but no apoptosis was induced in the β-catenin wild-type cell lines A375 and HT29 by the treatment with PD184352 at such concentrations that the phosphorylation of ERK was completely inhibited, i.e., 0.30 µM and 3.0 µM, respectively. Apoptosis was induced in A375 by the treatment with PD184352 at a concentration higher than such a concentration that the phosphorylation of ERK was completely inhibited, which was considered to result from the fact that PD184352 at a high concentration exhibits inhibitory effects on members of the MEK family such as MEK5 as well as MEK1/2, that is to say, to be caused by a factor other than the inhibition of the canonical MAPK signaling pathway in which MEK1/2 are involved. PD184352 did not exhibit any particular influence on the APC mutant cell line DLD-1 at such a concentration that the phosphorylation of ERK was completely inhibited, i.e., 10 µM.

Next, the treatment with the Raf inhibitor sorafenib did not provide complete inhibitory effects on the phosphorylation of MEK and ERK in any of the cell lines. Therefore, the evaluation of the apoptosis-inducing activity of sorafenib was considered impossible.

The results revealed that the MAPK signaling pathway inhibitor, in particular, the canonical MAPK signaling pathway inhibitor had active β-catenin mutant cell-selective apoptosis-inducing activity, as with SMK-17.

EXAMPLE 4

The results of Examples 1 to 3 showed that the active β-catenin mutation was a sensitivity-determining factor for the apoptosis induction by the MAPK signaling pathway inhibitor. In view of the foregoing, the involvement of the Wnt/β-catenin signaling pathway in the apoptosis induction by SMK-17 was investigated by a loss-of-function test.

The loss-of-function test was performed by evaluating an influence on the apoptosis-inducing activity of SMK-17 in cells in which the Wnt/β-catenin signaling pathway was inactivated by the knockdown of β-catenin or the forced expression of DN-TCF4. Cells without the knockdown of β-catenin or the forced expression of DN-TCF4 were used as control cells.

First, an attempt was made to perform the knockdown of β-catenin by siRNA in the active β-catenin mutant cell line HCT_116 in which apoptosis was induced by the treatment with SMK-17. The knockdown was performed by a reverse transfection method. The cells were collected after 24, 48, 72, 96 hours, and the expression amount of β-catenin was detected by western blotting. As a result, it was confirmed that the expression of β-catenin was decreased 48 hours after the knockdown (panel A of FIG. 4). Next, the apoptosis-inducing activity of SMK-17 was evaluated by treating the cells with 3.0 µM SMK-17 48 hours after the knockdown and detecting a sub-G1 population using a flow cytometer after 48 hours.

Figure 4:
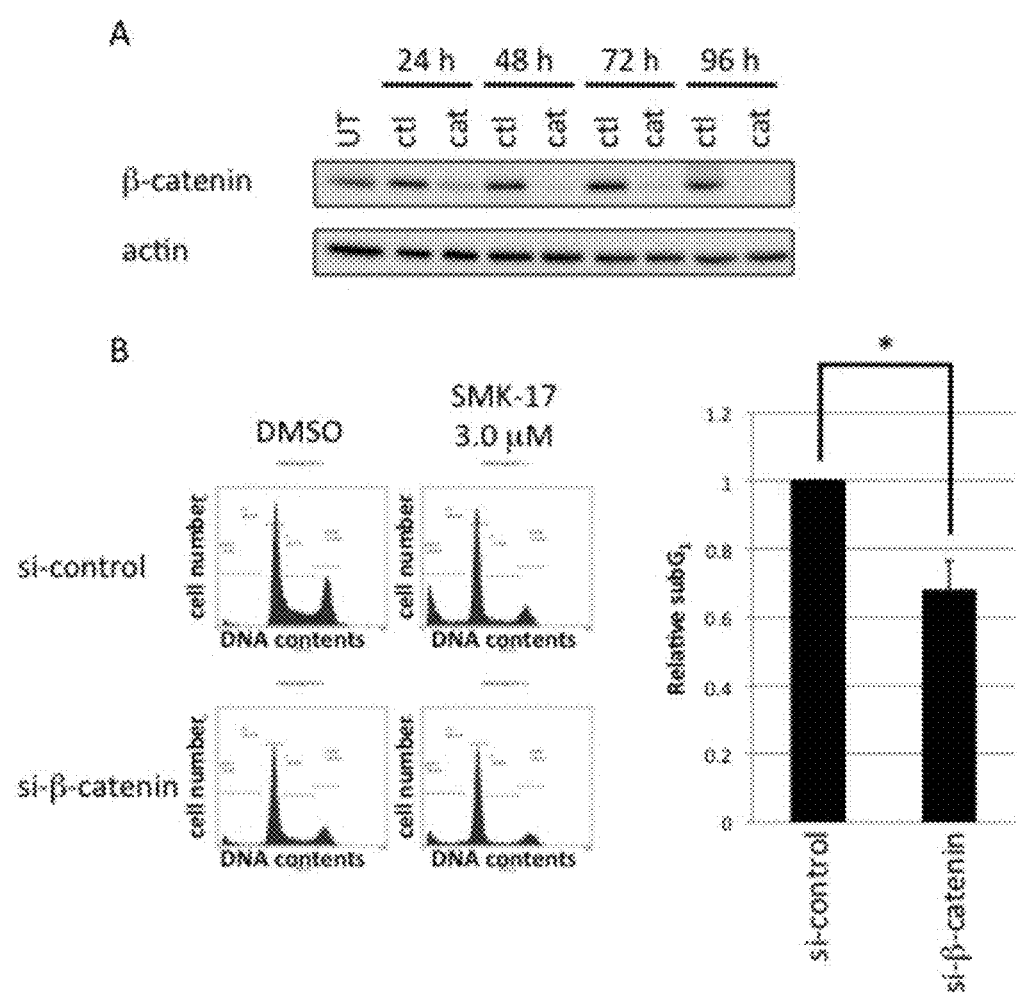
FIG. 4 shows that the apoptosis-inducing activity of SMK-17 was significantly suppressed in cells in which β-catenin was knocked down by β-catenin siRNA. The panel A shows that the decreased expression of β-catenin was confirmed 48 hours after the knockdown. In the panel A, "cat" represents β-catenin siRNA, and "ctl" represents control siRNA. Actin was used as an internal standard. The panel B shows that the apoptosis-inducing activity of SMK-17 was significantly suppressed in cells in which β-catenin was knocked down as compared to cells treated with control siRNA. In the panel B, "si-β-catenin" represents β-catenin siRNA, and "si-control" represents control siRNA (Example 4).

As a result, the apoptosis-inducing activity of SMK-17 was significantly suppressed in the β-catenin-knockdown cells as compared to the control cells (panel B of FIG. 4).

Next, DN-TCF4 was forcedly expressed in the active β-catenin mutant cell line HCT_116 to evaluate the apoptosis-inducing activity of SMK-17. DN-TCF4 is being deficient in amino acids at positions 1 to 31 of the DNA binding site of TCF4, and hence cannot bind to DNA even when β-catenin binds thereto. Thus, transcription by wild-type TCF4 is not promoted. That is, the Wnt/β-catenin signaling pathway can be brought into an inactivated state by the forced expression of DN-TCF4. Cells without forced expression of DN-TCF4 were used as control cells.

Specifically, in the same manner as in the above-mentioned siRNA transfection method, the HCT_116 cells were transfected with DN-TCF4 and evaluated for TCF4 transcriptional activity by a TOPFLASH reporter assay. TOPFLASH, in which firefly luciferase is inserted downstream of the DNA binding sequence of TCF4, expresses firefly luciferase by the binding of TCF4. Thus, the TCF4 transcriptional activity can be evaluated by the light emission amount of firefly luciferase. In addition, for correction of the comparison between cell lines, cells were transfected with a renilla luciferase reporter plasmid, and the comparison between cell lines was performed using a value obtained by calculating the light emission amount of firefly luciferase relative to the light emission amount of renilla luciferase constitutively expressed by a TK-promoter.

Figure 5:
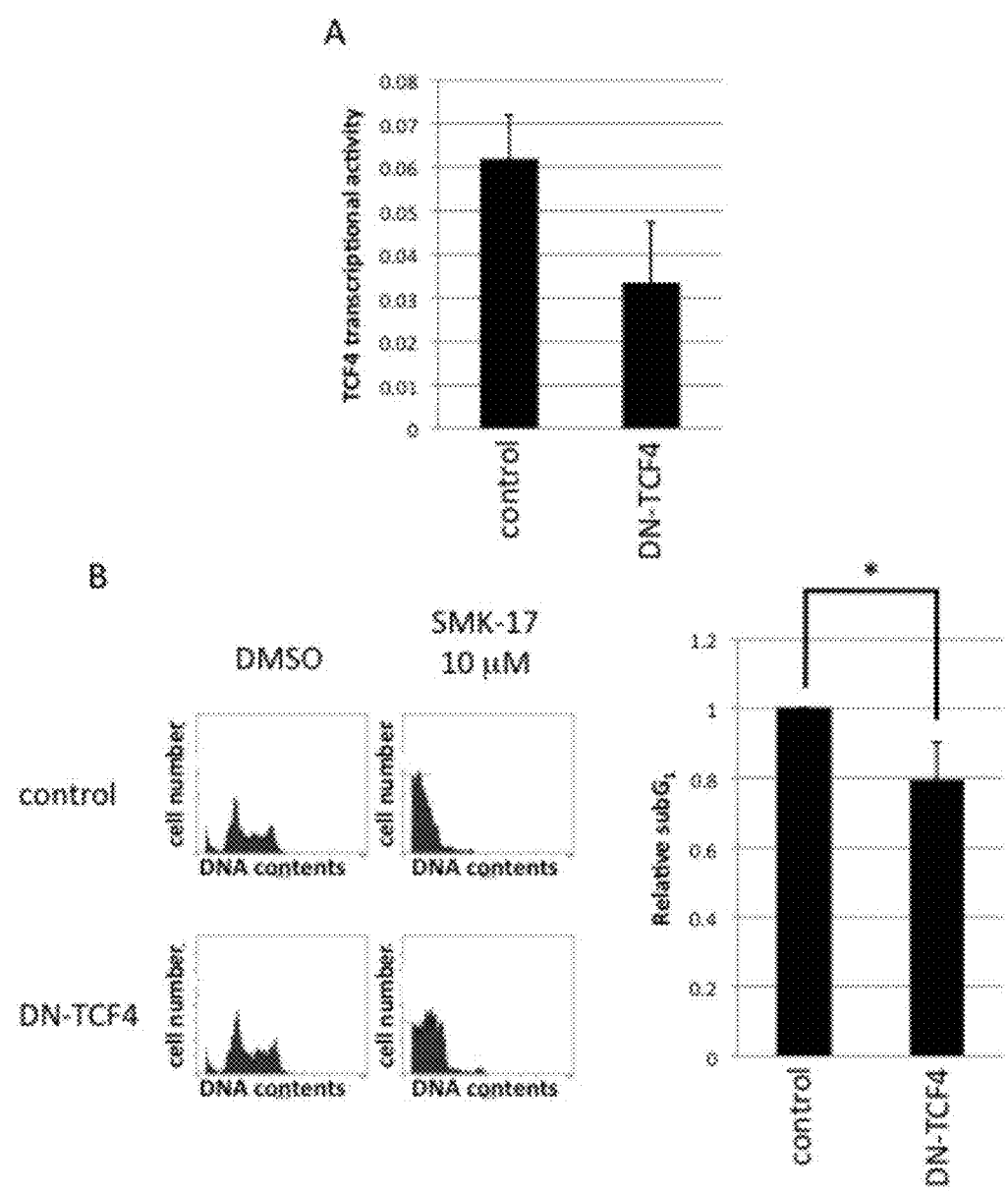
FIG. 5 shows that the apoptosis-inducing activity of SMK-17 was suppressed by suppressing a Wnt/β-catenin signaling pathway by the forced expression of dominant-negative TCF4 (DN-TCF4). The panel A shows that TCF4 transcriptional activity was suppressed by the forced expression of DN-TCF4 as compared to a control. The left picture of the panel B shows that the number of sub-G1 cells was increased by treatment with SMK-17 in control cells, whereas the increase in number of sub-G1 cells by the treatment with SMK-17 observed in the control cells was suppressed in cells with forced expression of DN-TCF4. The right picture of the panel B shows that the relative number of sub-G1 cells was significantly reduced in the cells with forced expression of DN-TCF4 as compared to the control cells when the cells were treated with SMK-17 (Example 4).

As a result of the TOPFLASH reporter assay, it was confirmed that the TCF4 transcriptional activity was suppressed by the forced expression of DN-TCF4 (panel A of FIG. 5). Next, the apoptosis-inducing activity of SMK-17 was evaluated by treating the cells with SMK-17 at a concentration of 10 µM and detecting a sub-G1 population using a flow cytometer after 48 hours. As a result, the apoptosis induction by SMK-17 was significantly suppressed in the cells in which DN-TCF4 was forcedly expressed as compared to the control cells (panel B of FIG. 5).

EXAMPLE 5

The results of Examples 1 to 3 showed that the active β-catenin mutation was a sensitivity-determining factor for the apoptosis induction by the MAPK signaling pathway inhibitor. In view of the foregoing, the involvement of the Wnt/β-catenin signaling pathway in the apoptosis induction by SMK-17 was investigated by a gain-of-function test.

In the gain-of-function test, the β-catenin wild-type cell line A375 was used, whose apoptosis was not induced even when the cells were treated with SMK-17. The Wnt/β-catenin signaling pathway was activated by making active β-catenin forcedly express in the cells, or stimulating the cells with wnt3a that is a ligand for Fz, and an influence thereof on the apoptosis-inducing activity of SMK-17 was evaluated.

Figure 6:
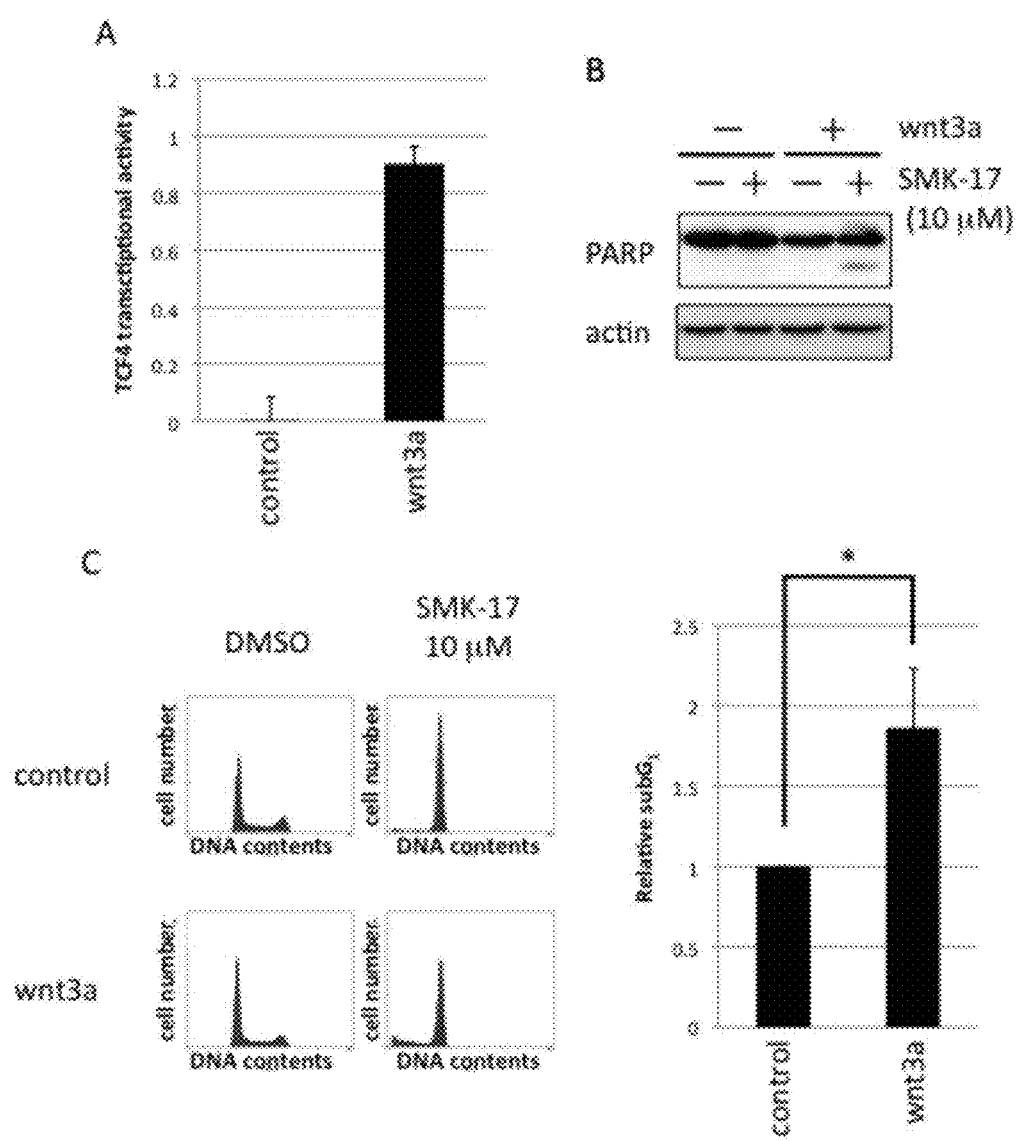
FIG. 6 shows that the apoptosis-inducing activity of SMK-17 was observed by stimulating a Wnt/β-catenin signaling pathway with a Wnt ligand wnt3a. The panel A shows that TCF4 transcriptional activity was increased by wnt3a stimulation in a cell line having wild-type β-catenin, A375. The panel B shows that the cleavage of poly(ADP-ribose) polymerase (hereinafter abbreviated as PARP) was induced by treatment with SMK-17 under wnt3a stimulation condition. The panel C shows that the number of sub-G1 cells was significantly increased in A375 by treatment with SMK-17 under wnt3a stimulation condition, but no increase in number of sub-G1 cells was observed under no wnt3a stimulation condition (Example 5).

First, the A375 cells were stimulated with wnt3a. Wnt3a binds to Fz present on a membrane surface, and inhibits the phosphorylation of GSK-3 via Axin, thereby suppressing the formation of a complex that degrades β-catenin. This allows the Wnt/β-catenin signaling pathway to be activated. Specifically, the A375 cells transfected with TOPFLASH and renilla luciferase reporter plasmids were treated with wnt3a (50 ng/mL) and evaluated for TCF4 transcriptional activity after 24 hours by a TOPFLASH reporter assay. As a result, the TCF4 transcriptional activity was found to be increased by the wnt3a stimulation (panel A of FIG. 6).

In addition, the cells stimulated with wnt3a were treated with SMK-17 (10 μM), followed by measuring the cleavage of PARP after 24 hours by western blotting, and evaluating the apoptosis-inducing activity after 48 hours by detecting a sub-G1 population using a flow cytometer. The A375 cells without stimulation with wnt3a were used as control cells. As a result, the cleavage of PARP was not observed in the case of SMK-17 alone, whereas the cleavage of PARP was induced under the wnt3a stimulation condition (panel B of FIG. 6). In addition, the apoptosis-inducing activity of SMK-17 was significantly promoted in the cells stimulated with wnt3a as compared to the control cells (panel C of FIG. 6).

Figure 7:
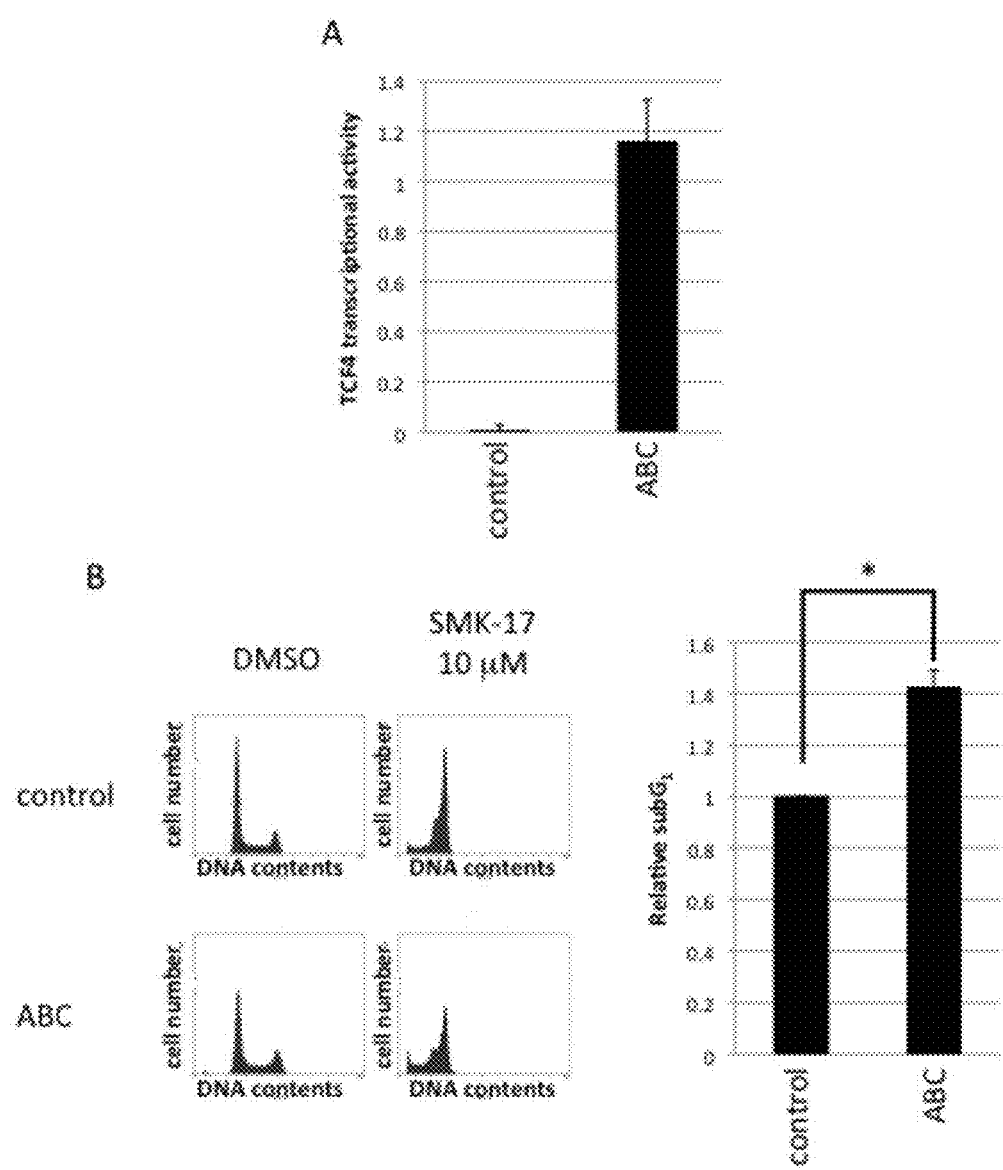
FIG. 7 shows that forced expression of active β-catenin in a cell line having wild-type β-catenin, A375, resulted in observation of apoptosis induction by SMK-17.

Next, active β-catenin was forcedly expressed in the A375 cells to evaluate the apoptosis-inducing activity of SMK-17. Because of having mutations at a β-catenin phosphorylation site, that is, a substitution of serine to alanine at position 37 (S37A) and a substitution of serine to alanine at position 45 (S45A), active β-catenin to be forcedly expressed enters the nucleus to enhance a signal without being phosphorylated by the complex, thereby activating the Wnt/β-catenin signaling pathway. The A375 cells were transfected with active β-catenin to evaluate TCF4 transcriptional activity by a TOPFLASH reporter assay. The A375 cells not transfected with active β-catenin were used as control cells. As a result, the TCF4 transcriptional activity was found to be increased by the forced expression of active β-catenin (panel A of FIG. 7).

In addition, the cells were treated with SMK-17 (10 μM), and the apoptosis-inducing activity after 48 hours was evaluated by detecting a sub-G1 population using a flow cytometer. As a result, the apoptosis-inducing activity of SMK-17 was significantly promoted in the cells in which active β-catenin was forcedly expressed as compared to the control cells (panel B of FIG. 7).

Both the loss-of-function test and gain-of-function test of Example 4 and Example 5 suggested that the Wnt/β-catenin signaling pathway was involved in the active β-catenin mutant cell-selective apoptosis induction by the MEK inhibitor SMK-17.

EXAMPLE 6

The in vivo effect of SMK-17 was evaluated. Specifically, tumor cells were cultured in vitro, and collected using trypsin EDTA and PBS⁻ on the day of transplantation into mice. The collected cells were resuspended at $1\times10^8$ cells/mL in PBS⁻, and 0.1 mL of the cell suspension was transplanted subcutaneously into the axillar region of Balb/c-nu/nu mice (CLEA Japan, Inc.). After confirmation of tumor engraftment in the mice, a liquid for administration in which a test compound was suspended in a 0.5% MC aqueous solution (manufactured by Wako Pure Chemical Industries, Ltd.) was orally administered to the mice at an intended dose, and the tumor volume was measured time dependently with an electronic caliper (manufactured by Mitutoyo Corporation).

The level of apoptosis of tumor cells in a tumor tissue was measured by a TdT-mediated dUTP-biotin nick end labeling (TUNEL) method. This measurement was performed using a commercially available TUNEL measurement kit (manufactured by CHEMICON) according to the recommended protocol included with the kit.

Figure 8:
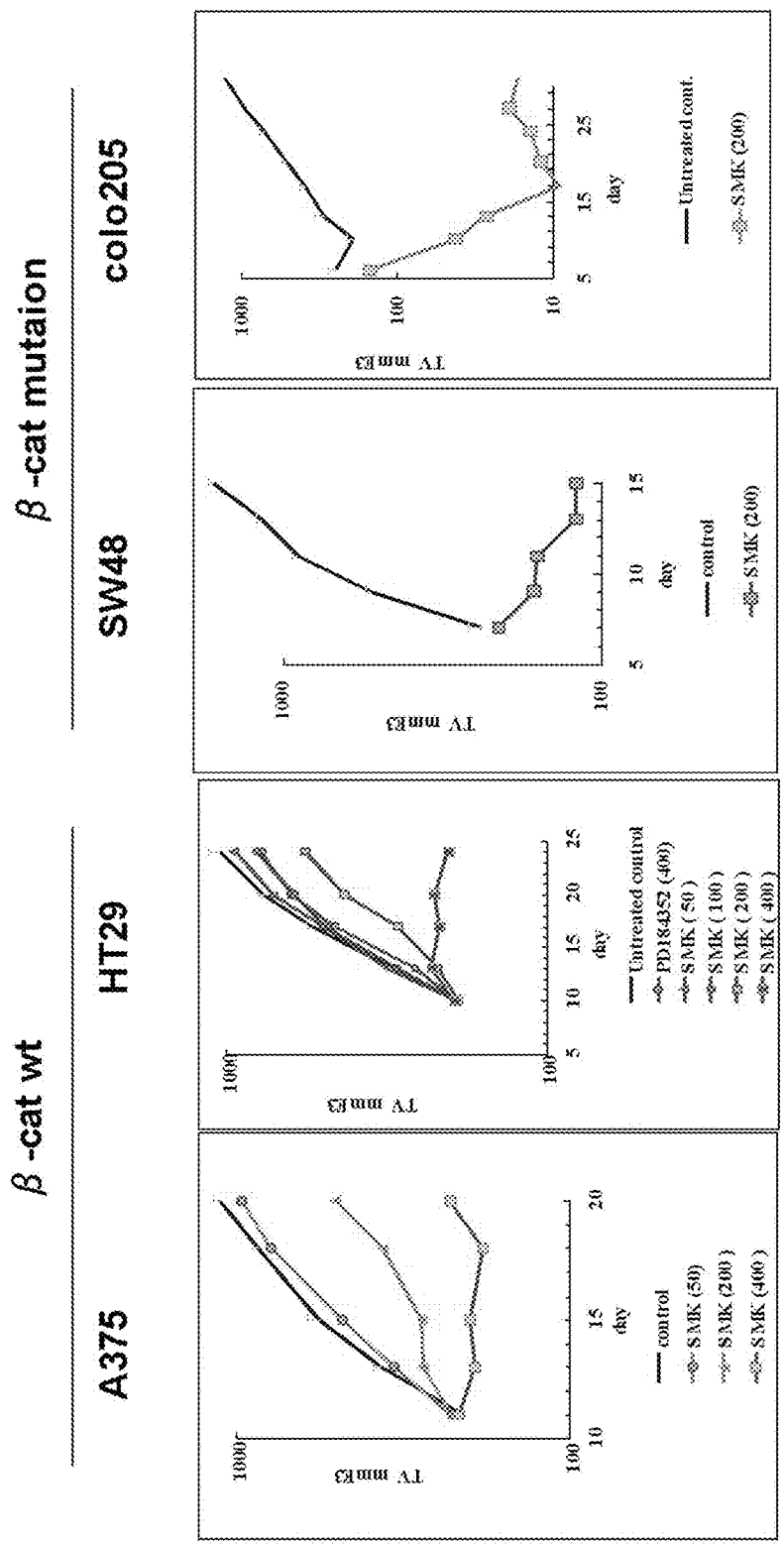
FIG. 8 shows that SMK-17 exhibited a tumor regression effect in vivo. A decrease in tumor volume (represented by "TV" in FIG. 8) was observed by the administration of SMK-17 in each of nude mice bearing tumor cell lines having active β-catenin mutations, SW48 and colo205. On the other hand, a tumor growth-suppressing effect was observed by the administration of SMK-17 in each of nude mice bearing cell lines having wild-type β-catenin, A375 and HT29, but not observed tumor regression effect (Example 6).

As shown in FIG. 8, SMK-17 exhibited a tumor regression effect in vivo. Specifically, a decrease in tumor volume was observed in the nude mice bearing the tumor cell line SW48 that had an active β-catenin mutation, when SMK-17 at 200 mg/kg was orally administered to the mice. Similarly, a decrease in tumor volume was observed in the nude mice bearing the tumor cell line colo205 that had an active β-catenin mutation, when SMK-17 at 200 mg/kg was administered to the mice.

On the other hand, a suppressing effect on an increase in tumor volume was observed but no tumor regression effect was found in the nude mice bearing the tumor cell line A375 or HT29 that had wild-type β-catenin, when SMK-17 at 200 mg/kg was administered to the mice.

Figure 9:
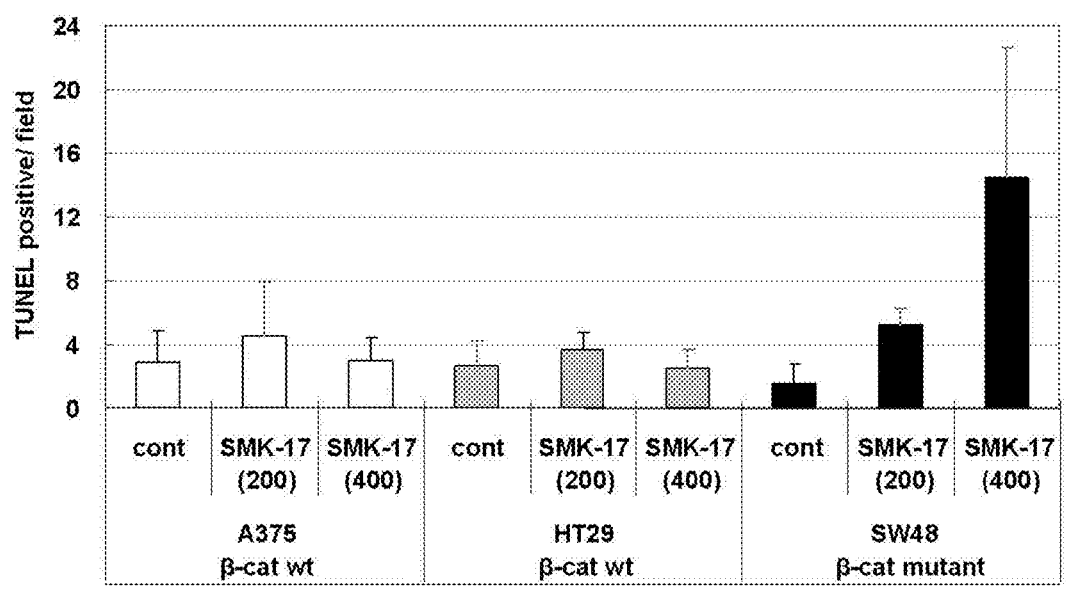
FIG. 9 shows that the number of apoptosis-positive cells was increased by the administration of SMK-17 in a tumor tissue of nude mice bearing a tumor cell line having an active β-catenin mutation, SW48. No change was observed in number of apoptosis-positive cells by the administration of SMK-17 in a tumor tissue in each of nude mice bearing cell lines having wild-type β-catenin, A375 and HT29.

In addition, the number of apoptosis-positive cells in a tumor tissue was found to be increased in the nude mice bearing the SW48 cells, when SMK-17 was administered to the mice (FIG. 9). On the other hand, no change was observed in the number of apoptosis-positive cells in a tumor tissue in the nude mice bearing A375 cells or HT29 cells, even when SMK-17 was administered to the mice.

The results revealed that SMK-17 exhibited a regression effect on the tumor that has an active β-catenin mutation in vivo, and the tumor regression effect was due to an inducing effect on the apoptosis of the tumor cells.

INDUSTRIAL APPLICABILITY

As described above, the present invention provides a method of predicting responsiveness to cancer disease treatment with a compound that inhibits a MAPK signaling pathway, and a method of selecting a patient who is determined to have high responsiveness to the administration of a drug containing the compound, and thereby allows a cancer disease to be effectively treated with a compound that inhibits a MAPK signaling pathway. Thus, the present invention is extremely useful in the therapeutic field of a cancer patient.

What is claimed is:

1. A method of treating a cancer disease, comprising:
    using a biological sample derived from a cancer patient, measuring whether β-catenin contained in the biological sample has at least one kind of a mutation selected from the group consisting of (i) an active mutation and (ii) a substitution mutation of an asparagine residue to a serine residue at position 287;
    selecting a patient who is detected to have the mutation in β-catenin as a patient to be subjected to cancer disease treatment with a means for inhibiting MEK1/2, wherein the patient has a cancer disease selected from colorectal cancer, skin cancer, lung cancer, or adrenal cortex cancer; and
    administering a therapeutically effective amount of the means for inhibiting MEK1/2 to the selected patient.

2. The method according to claim 1, wherein the active mutation comprises at least one mutation selected from the following:
    (1) a substitution mutation of a serine residue at position 33, a serine residue at position 37, a threonine residue at position 41, or a serine residue at position 45 in an amino acid sequence of β-catenin to an amino acid residue other than a serine residue or a threonine residue; and
    (2) a deletion mutation of a serine residue at position 33, a serine residue at position 37, a threonine residue at position 41, or a serine residue at position 45 in an amino acid sequence of β-catenin.

3. The method according to claim 1, wherein the active mutation is at least one mutation selected from the following:

(3) a substitution mutation of a serine residue at position 33 or a serine residue at position 45 in an amino acid sequence of β-catenin to an amino acid residue other than a serine residue or a threonine residue; and (4) a deletion mutation of a serine residue at position 45 in an amino acid sequence of β-catenin.

4. The method according to claim 1, wherein the biological sample is a biological sample containing a cancer cell or a cancer tissue.

5. The method according to claim 1, wherein the cancer patient has a cancer disease selected from colorectal cancer or skin cancer.

* * * * *

SEQUENCE LISTING

<160> NUMBER OF SEQ ID NOS: 3

<210> SEQ ID NO 1
<211> LENGTH: 2346
<212> TYPE: DNA
<213> ORGANISM: Homo sapiens
<220> FEATURE:
<221> NAME/KEY: CDS
<222> LOCATION: (1)..(2346)
<220> FEATURE:
<221> NAME/KEY: misc_feature
<223> OTHER INFORMATION: gene encoding a beta-catenin (SEQ ID NO.: 2)

<400> SEQUENCE: 1

| | | | | | | | | | | | | | | | | |
|---|---|---|---|---|---|---|---|---|---|---|---|---|---|---|---|---|
| atg | gct | act | caa | gct | gat | ttg | atg | gag | ttg | gac | atg | gcc | atg | gaa | cca | 48 |
| Met | Ala | Thr | Gln | Ala | Asp | Leu | Met | Glu | Leu | Asp | Met | Ala | Met | Glu | Pro | |
| 1 | | | | 5 | | | | | 10 | | | | | 15 | | |
| gac | aga | aaa | gcg | gct | gtt | agt | cac | tgg | cag | caa | cag | tct | tac | ctg | gac | 96 |
| Asp | Arg | Lys | Ala | Ala | Val | Ser | His | Trp | Gln | Gln | Gln | Ser | Tyr | Leu | Asp | |
| | | | 20 | | | | | 25 | | | | | 30 | | | |
| tct | gga | atc | cat | tct | ggt | gcc | act | aca | aca | gct | cct | tct | ctg | agt | ggt | 144 |
| Ser | Gly | Ile | His | Ser | Gly | Ala | Thr | Thr | Thr | Ala | Pro | Ser | Leu | Ser | Gly | |
| | | | 35 | | | | | 40 | | | | | 45 | | | |
| aaa | ggc | aat | cct | gag | gaa | gag | gat | gtg | gat | acc | tcc | caa | gtc | ctg | tat | 192 |
| Lys | Gly | Asn | Pro | Glu | Glu | Glu | Asp | Val | Asp | Thr | Ser | Gln | Val | Leu | Tyr | |
| | 50 | | | | | 55 | | | | | 60 | | | | | |
| gag | tgg | gaa | cag | gga | ttt | tct | cag | tcc | ttc | act | caa | gaa | caa | gta | gct | 240 |
| Glu | Trp | Glu | Gln | Gly | Phe | Ser | Gln | Ser | Phe | Thr | Gln | Glu | Gln | Val | Ala | |
| 65 | | | | | 70 | | | | | 75 | | | | | 80 | |
| gat | att | gat | gga | cag | tat | gca | atg | act | cga | gct | cag | agg | gta | cga | gct | 288 |
| Asp | Ile | Asp | Gly | Gln | Tyr | Ala | Met | Thr | Arg | Ala | Gln | Arg | Val | Arg | Ala | |
| | | | | 85 | | | | | 90 | | | | | 95 | | |
| gct | atg | ttc | cct | gag | aca | tta | gat | gag | ggc | atg | cag | atc | cca | tct | aca | 336 |
| Ala | Met | Phe | Pro | Glu | Thr | Leu | Asp | Glu | Gly | Met | Gln | Ile | Pro | Ser | Thr | |
| | | | 100 | | | | | 105 | | | | | 110 | | | |
| cag | ttt | gat | gct | gct | cat | ccc | act | aat | gtc | cag | cgt | ttg | gct | gaa | cca | 384 |
| Gln | Phe | Asp | Ala | Ala | His | Pro | Thr | Asn | Val | Gln | Arg | Leu | Ala | Glu | Pro | |
| | | 115 | | | | | 120 | | | | | 125 | | | | |
| tca | cag | atg | ctg | aaa | cat | gca | gtt | gta | aac | ttg | att | aac | tat | caa | gat | 432 |
| Ser | Gln | Met | Leu | Lys | His | Ala | Val | Val | Asn | Leu | Ile | Asn | Tyr | Gln | Asp | |
| | 130 | | | | | 135 | | | | | 140 | | | | | |
| gat | gca | gaa | ctt | gcc | aca | cgt | gca | atc | cct | gaa | ctg | aca | aaa | ctg | cta | 480 |
| Asp | Ala | Glu | Leu | Ala | Thr | Arg | Ala | Ile | Pro | Glu | Leu | Thr | Lys | Leu | Leu | |
| 145 | | | | | 150 | | | | | 155 | | | | | 160 | |
| aat | gac | gag | gac | cag | gtg | gtg | gtt | aat | aag | gct | gca | gtt | atg | gtc | cat | 528 |
| Asn | Asp | Glu | Asp | Gln | Val | Val | Val | Asn | Lys | Ala | Ala | Val | Met | Val | His | |
| | | | | 165 | | | | | 170 | | | | | 175 | | |
| cag | ctt | tct | aaa | aag | gaa | gct | tcc | aga | cac | gct | atc | atg | cgt | tct | cct | 576 |
| Gln | Leu | Ser | Lys | Lys | Glu | Ala | Ser | Arg | His | Ala | Ile | Met | Arg | Ser | Pro | |
| | | | 180 | | | | | 185 | | | | | 190 | | | |
| cag | atg | gtg | tct | gct | att | gta | cgt | acc | atg | cag | aat | aca | aat | gat | gta | 624 |
| Gln | Met | Val | Ser | Ala | Ile | Val | Arg | Thr | Met | Gln | Asn | Thr | Asn | Asp | Val | |
| | | 195 | | | | | 200 | | | | | 205 | | | | |
| gaa | aca | gct | cgt | tgt | acc | gct | ggg | acc | ttg | cat | aac | ctt | tcc | cat | cat | 672 |
| Glu | Thr | Ala | Arg | Cys | Thr | Ala | Gly | Thr | Leu | His | Asn | Leu | Ser | His | His | |
| | 210 | | | | | 215 | | | | | 220 | | | | | |
| cgt | gag | ggc | tta | ctg | gcc | atc | ttt | aag | tct | gga | ggc | att | cct | gcc | ctg | 720 |
| Arg | Glu | Gly | Leu | Leu | Ala | Ile | Phe | Lys | Ser | Gly | Gly | Ile | Pro | Ala | Leu | |
| 225 | | | | | 230 | | | | | 235 | | | | | 240 | |
| gtg | aaa | atg | ctt | ggt | tca | cca | gtg | gat | tct | gtg | ttg | ttt | tat | gcc | att | 768 |
| Val | Lys | Met | Leu | Gly | Ser | Pro | Val | Asp | Ser | Val | Leu | Phe | Tyr | Ala | Ile | |
| | | | | 245 | | | | | 250 | | | | | 255 | | |

```
aca act ctc cac aac ctt tta tta cat caa gaa gga gct aaa atg gca       816
Thr Thr Leu His Asn Leu Leu Leu His Gln Glu Gly Ala Lys Met Ala
            260                 265                 270 gtg cgt tta gct ggt ggg ctg cag aaa atg gtt gcc ttg ctc aac aaa       864
Val Arg Leu Ala Gly Gly Leu Gln Lys Met Val Ala Leu Leu Asn Lys
        275                 280                 285 aca aat gtt aaa ttc ttg gct att acg aca gac tgc ctt caa att tta       912
Thr Asn Val Lys Phe Leu Ala Ile Thr Thr Asp Cys Leu Gln Ile Leu
    290                 295                 300 gct tat ggc aac caa gaa agc aag ctc atc ata ctg gct agt ggt gga       960
Ala Tyr Gly Asn Gln Glu Ser Lys Leu Ile Ile Leu Ala Ser Gly Gly
305                 310                 315                 320 ccc caa gct tta gta aat ata atg agg acc tat act tac gaa aaa cta      1008
Pro Gln Ala Leu Val Asn Ile Met Arg Thr Tyr Thr Tyr Glu Lys Leu
                325                 330                 335 ctg tgg acc aca agc aga gtg ctg aag gtg cta tct gtc tgc tct agt      1056
Leu Trp Thr Thr Ser Arg Val Leu Lys Val Leu Ser Val Cys Ser Ser
            340                 345                 350 aat aag ccg gct att gta gaa gct ggt gga atg caa gct tta gga ctt      1104
Asn Lys Pro Ala Ile Val Glu Ala Gly Gly Met Gln Ala Leu Gly Leu
        355                 360                 365 cac ctg aca gat cca agt caa cgt ctt gtt cag aac tgt ctt tgg act      1152
His Leu Thr Asp Pro Ser Gln Arg Leu Val Gln Asn Cys Leu Trp Thr
    370                 375                 380 ctc agg aat ctt tca gat gct gca act aaa cag gaa ggg atg gaa ggt      1200
Leu Arg Asn Leu Ser Asp Ala Ala Thr Lys Gln Glu Gly Met Glu Gly
385                 390                 395                 400 ctc ctt ggg act ctt gtt cag ctt ctg ggt tca gat gat ata aat gtg      1248
Leu Leu Gly Thr Leu Val Gln Leu Leu Gly Ser Asp Asp Ile Asn Val
                405                 410                 415 gtc acc tgt gca gct gga att ctt tct aac ctc act tgc aat aat tat      1296
Val Thr Cys Ala Ala Gly Ile Leu Ser Asn Leu Thr Cys Asn Asn Tyr
            420                 425                 430 aag aac aag atg atg gtc tgc caa gtg ggt ggt ata gag gct ctt gtg      1344
Lys Asn Lys Met Met Val Cys Gln Val Gly Gly Ile Glu Ala Leu Val
        435                 440                 445 cgt act gtc ctt cgg gct ggt gac agg gaa gac atc act gag cct gcc      1392
Arg Thr Val Leu Arg Ala Gly Asp Arg Glu Asp Ile Thr Glu Pro Ala
    450                 455                 460 atc tgt gct ctt cgt cat ctg acc agc cga cac caa gaa gca gag atg      1440
Ile Cys Ala Leu Arg His Leu Thr Ser Arg His Gln Glu Ala Glu Met
465                 470                 475                 480 gcc cag aat gca gtt cgc ctt cac tat gga cta cca gtt gtg gtt aag      1488
Ala Gln Asn Ala Val Arg Leu His Tyr Gly Leu Pro Val Val Val Lys
                485                 490                 495 ctc tta cac cca cca tcc cac tgg cct ctg ata aag gct act gtt gga      1536
Leu Leu His Pro Pro Ser His Trp Pro Leu Ile Lys Ala Thr Val Gly
            500                 505                 510 ttg att cga aat ctt gcc ctt tgt ccc gca aat cat gca cct ttg cgt      1584
Leu Ile Arg Asn Leu Ala Leu Cys Pro Ala Asn His Ala Pro Leu Arg
        515                 520                 525 gag cag ggt gcc att cca cga cta gtt cag ttg ctt gtt cgt gca cat      1632
Glu Gln Gly Ala Ile Pro Arg Leu Val Gln Leu Leu Val Arg Ala His
    530                 535                 540 cag gat acc cag cgc cgt acg tcc atg ggt ggg aca cag cag caa ttt      1680
Gln Asp Thr Gln Arg Arg Thr Ser Met Gly Gly Thr Gln Gln Gln Phe
545                 550                 555                 560 gtg gag ggg gtc cgc atg gaa gaa ata gtt gaa ggt tgt acc gga gcc      1728
Val Glu Gly Val Arg Met Glu Glu Ile Val Glu Gly Cys Thr Gly Ala
```

-continued

```
                    565                 570                 575
ctt cac atc cta gct cgg gat gtt cac aac cga att gtt atc aga gga    1776
Leu His Ile Leu Ala Arg Asp Val His Asn Arg Ile Val Ile Arg Gly
            580                 585                 590 cta aat acc att cca ttg ttt gtg cag ctg ctt tat tct ccc att gaa    1824
Leu Asn Thr Ile Pro Leu Phe Val Gln Leu Leu Tyr Ser Pro Ile Glu
            595                 600                 605 aac atc caa aga gta gct gca ggg gtc ctc tgt gaa ctt gct cag gac    1872
Asn Ile Gln Arg Val Ala Ala Gly Val Leu Cys Glu Leu Ala Gln Asp
610                 615                 620 aag gaa gct gca gaa gct att gaa gct gag gga gcc aca gct cct ctg    1920
Lys Glu Ala Ala Glu Ala Ile Glu Ala Glu Gly Ala Thr Ala Pro Leu
625                 630                 635                 640 aca gag tta ctt cac tct agg aat gaa ggt gtg gcg aca tat gca gct    1968
Thr Glu Leu Leu His Ser Arg Asn Glu Gly Val Ala Thr Tyr Ala Ala
                645                 650                 655 gct gtt ttg ttc cga atg tct gag gac aag cca caa gat tac aag aaa    2016
Ala Val Leu Phe Arg Met Ser Glu Asp Lys Pro Gln Asp Tyr Lys Lys
            660                 665                 670 cgg ctt tca gtt gag ctg acc agc tct ctc ttc aga aca gag cca atg    2064
Arg Leu Ser Val Glu Leu Thr Ser Ser Leu Phe Arg Thr Glu Pro Met
        675                 680                 685 gct tgg aat gag act gct gat ctt gga ctt gat att ggt gcc cag gga    2112
Ala Trp Asn Glu Thr Ala Asp Leu Gly Leu Asp Ile Gly Ala Gln Gly
        690                 695                 700 gaa ccc ctt gga tat cgc cag gat gat cct agc tat cgt tct ttt cac    2160
Glu Pro Leu Gly Tyr Arg Gln Asp Asp Pro Ser Tyr Arg Ser Phe His
705                 710                 715                 720 tct ggt gga tat ggc cag gat gcc ttg ggt atg gac ccc atg atg gaa    2208
Ser Gly Gly Tyr Gly Gln Asp Ala Leu Gly Met Asp Pro Met Met Glu
                725                 730                 735 cat gag atg ggt ggc cac cac cct ggt gct gac tat cca gtt gat ggg    2256
His Glu Met Gly Gly His His Pro Gly Ala Asp Tyr Pro Val Asp Gly
            740                 745                 750 ctg cca gat ctg ggg cat gcc cag gac ctc atg gat ggg ctg cct cca    2304
Leu Pro Asp Leu Gly His Ala Gln Asp Leu Met Asp Gly Leu Pro Pro
        755                 760                 765 ggt gac agc aat cag ctg gcc tgg ttt gat act gac ctg taa            2346
Gly Asp Ser Asn Gln Leu Ala Trp Phe Asp Thr Asp Leu
770                 775                 780
```

<210> SEQ ID NO 2
<211> LENGTH: 781
<212> TYPE: PRT
<213> ORGANISM: Homo sapiens

<400> SEQUENCE: 2

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
                20                  25                  30

Ser Gly Ile His Ser Gly Ala Thr Thr Thr Ala Pro Ser Leu Ser Gly
            35                  40                  45

Lys Gly Asn Pro Glu Glu Glu Asp Val Asp Thr Ser Gln Val Leu Tyr
        50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

```
Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
            115                 120                 125

Ser Gln Met Leu Lys His Ala Val Val Asn Leu Ile Asn Tyr Gln Asp
            130                 135                 140

Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
            195                 200                 205

Glu Thr Ala Arg Cys Thr Ala Gly Thr Leu His Asn Leu Ser His His
            210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
            290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
            370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
            435                 440                 445

Arg Thr Val Leu Arg Ala Gly Asp Arg Glu Asp Ile Thr Glu Pro Ala
            450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510
```

```
Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
        530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
            595                 600                 605

Asn Ile Gln Arg Val Ala Ala Gly Val Leu Cys Glu Leu Ala Gln Asp
        610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
            675                 680                 685

Ala Trp Asn Glu Thr Ala Asp Leu Gly Leu Asp Ile Gly Ala Gln Gly
            690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
            755                 760                 765

Gly Asp Ser Asn Gln Leu Ala Trp Phe Asp Thr Asp Leu
770                 775                 780

<210> SEQ ID NO 3
<211> LENGTH: 25
<212> TYPE: RNA
<213> ORGANISM: artificial
<220> FEATURE:
<223> OTHER INFORMATION: siRNA used in knoking down of beta-catenin gene

<400> SEQUENCE: 3
auuacuagag cagacagaua gcacc                                         25
```